US012679812B2

(12) United States Patent
Babich et al.

(10) Patent No.: US 12,679,812 B2
(45) Date of Patent: Jul. 14, 2026

(54) $^{18}$F-LABELED TRIAZOLE CONTAINING PSMA INHIBITORS

(71) Applicant: Cornell University, Ithaca, NY (US)

(72) Inventors: John W. Babich, New York, NY (US); James M. Kelly, New York, NY (US); Alejandro Amor-Coarasa, Ithaca, NY (US); Shashikanth Ponnala, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 17/390,284

(22) Filed: Jul. 30, 2021

(65) Prior Publication Data

US 2022/0194904 A1 Jun. 23, 2022

Related U.S. Application Data

(63) Continuation of application No. 16/233,026, filed on Dec. 26, 2018, now abandoned, which is a continuation of application No. 15/635,776, filed on Jun. 28, 2017, now abandoned.

(60) Provisional application No. 62/355,430, filed on Jun. 28, 2016.

(51) Int. Cl.

| | |
|---|---|
| ***C07D 249/06*** | (2006.01) |
| ***A61B 6/03*** | (2006.01) |
| ***A61K 9/00*** | (2006.01) |
| ***A61K 51/04*** | (2006.01) |
| ***C07C 275/16*** | (2006.01) |
| ***C07C 275/24*** | (2006.01) |

(52) U.S. Cl.

CPC ............ *C07D 249/06* (2013.01); *A61B 6/032* (2013.01); *A61B 6/037* (2013.01); *A61K 9/0019* (2013.01); *A61K 51/0497* (2013.01); *C07C 275/16* (2013.01); *C07C 275/24* (2013.01); *C07B 2200/05* (2013.01)

(58) Field of Classification Search

CPC ....... C07D 249/06; A61B 6/032; A61B 6/037; A61K 9/0019; A61K 51/0497; C07C 275/16; C07C 275/24

USPC ........................................................ 424/1.89

See application file for complete search history.

(56) References Cited

U.S. PATENT DOCUMENTS

| | | | |
|---|---|---|---|
| 5,672,662 | A | 9/1997 | Harris et al. |
| 2017/0326261 | A1 | 11/2017 | Oukhatar et al. |

FOREIGN PATENT DOCUMENTS

| | | | | |
|---|---|---|---|---|
| CA | 2998420 A1 | 6/2017 | | |
| CA | 3029273 A1 | 1/2018 | | |
| CA | 3117467 A1 | 4/2020 | | |
| CA | 3178858 A1 | 11/2021 | | |
| EP | 3 011 976 A1 | 4/2016 | | |
| WO | WO-2008058192 A2 * | 5/2008 | .......... | A61K 39/385 |
| WO | WO 2013/028664 A1 | 2/2013 | | |

(Continued)

OTHER PUBLICATIONS

Chen et al., "Novel molecular "add-on" based on Evans Blue confers superior pharmacokinetics and transforms drugs to theranostic agents," *Journal of Nuclear Medicine*, vol. 61, 44 pages (Nov. 22, 2016).

(Continued)

*Primary Examiner* — Michael G. Hartley
*Assistant Examiner* — Sean R Donohue
(74) *Attorney, Agent, or Firm* — Foley & Lardner LLP

(57) ABSTRACT

The present technology is directed to compounds, intermediates thereof, compositions thereof, medicaments thereof, and methods related to the imaging of mammalian tissue overexpressing PSMA. The compounds are of Formula I (I)

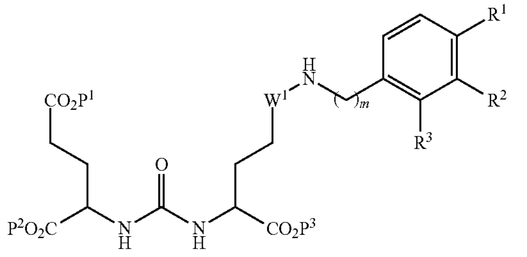

or a pharmaceutically acceptable salt thereof, wherein one of $R^1$, $R^2$, and $R^3$ is

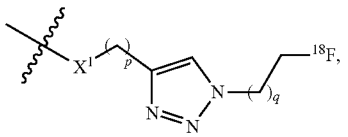

and of Formula IV (IV)

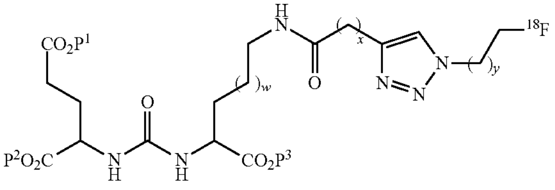

or a pharmaceutically acceptable salt thereof.

9 Claims, 6 Drawing Sheets

(56) References Cited

FOREIGN PATENT DOCUMENTS

| | | | |
|---|---|---|---|
| WO | WO-2016/062370 | | 4/2016 |
| WO | WO-2016/065145 | | 4/2016 |
| WO | WO 2017/027870 | | 2/2017 |
| WO | WO-2018/187631 | A1 | 10/2018 |

OTHER PUBLICATIONS

Thiele, "An Eighteen-Membered Macrocycficligand for Actinium-225Targeted AlphaTherapy," Angewandte Chemie International Edition, vol. 56, pp. 14712-14717 (2017).
Supplementary Search Report issue in European Patent Application No. 17821138.9, dated Jul. 23, 2020.
Kelly, et al., "Synthesis and pre-clinical evaluation of a new class of high-affinityI8F-labeled PSMA ligands for detection of prostate cancer by PET imaging", European Journal of Nuclear Medicine, vol. 44, No. 4, pp. 647-661 (Nov. 2016).
Non-Final Office Action issued in U.S. Appl. No. 16/233,026, dated Feb. 1, 2021.
Chen, et al., "[18F]Fluoroethyl Triazole Substitute PSMA Inhibitor Exhibiting Rapid Normal Organ Clearance," Bioconjugate Chemistry, vol. 27, pp. 1655-1662 (2016).
Amor-Coarasa, et al., "Comprehensive Quality Control of the ITG Ge-68/Ga-68 Generator and Synthesis of Ga-68-DOTATOC and GA-68-PSMA-HBED-CC for Clinical Imaging," Journal of Nuclear Medicine, Apr. 21, 2016.
Baccala, et al., "Expression of prostate-specific membrane antigen in tumor-associated neovasculature of renal neoplasms," Urology, vol. 70, Issue 2, Aug. 2007, pp. 385-390.
Boiocchi, et al., "Nature of Urea-Fluoride Interaction:? Incipient and Definitive Proton Transfer," Journal of the American Chemical Society, vol. 123, No. 50, Dec. 22, 2004, pp. 16507-16514.
Bouvet, et al., "Automated synthesis of [18F] DCFPyL via direct radiofluorination and validation in preclinical prostate cancer models," EJNMMI Research, vol. 6, No. 40, 2016.
Chang, et al., "Five different anti-prostate-specific membrane antigen (PSMA) antibodies confirm PSMA expression in tumor-associated neovasculature," Cancer Research, vol. 59, Issue 13, Jul. 1, 1999, pp. 3192-3198.
Chen, et al., "2-(3-{1-Carboxy-5-[(6-[18F]Fluoro-Pyridine-3-Carbonyl)-Amino]-Pentyl}-Ureido)-Pentanedioic Acid, [18F]DCFPyL, a PSMA-Based PET Imaging Agent for Prostate Cancer," Clinical Research Cancer, vol. 17, Issue 24, Dec. 2011, pp. 7645-7653.
Grootendorst, et al., "Cerenkov luminescence imaging (CLI) for image-guided cancer surgery," Clin Transl Imagine, vol. 4, Mar. 24, 2016, pp. 353-366.
Haffner, et al., "Prostate-specific membrane antigen expression in the neovasculature of gastric and colorectal cancers," Human Pathology, vol. 40, Issue 12, Dec. 2009, pp. 1754-1761.
Hillier, et al., "99mTc-Labeled Small-Molecule Inhibitors of Prostate-Specific Membrane Antigen for Molecular Imaging of Prostate Cancer," Journal of Nuclear Medicine, vol. 54, No. 8, Jun. 3, 2013, pp. 1369-1376.
International Search Report and Written Opinion issued on PCT/US2017/039710, mailed Nov. 2, 2017.
Maresca, et al., "A Series of Halogenated Heterodimeric Inhibitors of Prostate Specific Membrane Antigen (PSMA) as Radiolabeled Probes for Targeting Prostate Cancer," Journal of Medicinal Chemistry, vol. 52, 2009, pp. 347-357.
Nikolopoulou, et al., "Comparative evaluation of 68Ga-labeled urea-based PSMA ligands in LNCap tumor bearing mice," Journal of Nuclear Medicine, vol. 56, No. Supplement 3, May 1, 2015, p. 114.
Olberg, et al., "One Step of Radiosynthesis of 6-[(18)F]fluoronicotinic acid 2,3,5,6-tetrafluorophenyl ester ([(18)F]F-Py-TFP): a new prosthetic group for efficient labeling of biomolecules with fluorine-18," Journal of Medicinal Chemistry, vol. 53, Issue 4, Feb. 2010, pp. 1732-1740.
Robertson, et al., "Optical imaging of Cerenkov light generation from positron-emitting radiotracers," Phys Med Biol, vol. 54, Issue 16, 2009, pp. 355-365.
Samplaski, et al., "Folate hydrolase (prostate-specific membrane antigen) 1 expression in bladder cancer subtypes and associated tumor neovasculature," Modern Pathology, vol. 24, Issue 11, Nov. 2011, pp. 1521-1529.
Silver, "Prostate-specific Membrane Antigen Expression in Normal and Malignant Human Tissues," Clinical Cancer Research, vol. 3, Jan. 1997, pp. 81-85.
Tykvart, et al., "Rational design of urea-based glutamate carboxypeptidase II (GCPII) inhibitors as versatile tools for specific drug targeting and delivery," Bioorganic & Medicinal Chemistry, vol. 22, Issue 15, Aug. 2014, pp. 4099-4108.
Wang, et al., "Expression of prostate-specific membrane antigen in lung cancer cells and tumor neovasculature endothelial cells and its clinical significance," PLos One, vol. 10, No. 5, May 15, 2015, pp. 1-8.
Wernicke, et al., "Prostate-specific Membrane Antigen (PSMA) Expression in the Neovasculature of Gynecologic Malignancies: Implications for PSMA-targeted Therapy," Applied Immunohistochemistry & Molecular Morphology, vol. 25, No. 4, Feb. 9, 2016, pp. 271-276.
Wustemann, et al., "Design of Internalizing PSMA-specific Glu-ureido-based Radiotherapeuticals," Theranostics, Apr. 28, 2016, vol. 6, Issue 8, pp. 1085-1095.
Zhang, "An Ileal Crohn's Disease Gene Signature Based on Whole Human Genome Expression Profiles of Disease Unaffected Ileal Mucosal Biopises," PLos One, vol. 7, No. 5, May 14, 2012, pp. 1-8.
Organic Azides: Syntheses and Applications, edited by Stefan Brase and Klause Banert, 2010, pp. 1-27.
Organic Chemistry: Structure and Function, Vollhardt, K.P.C.; Schore, N.E.; W.H. Freeman and Company, New York, NY, 3rd Edition, 1999, p. 38.
Glaser et al., "Click Labeling with 2-[18F] Fluoroethylazide for Positron Emission Tomography," *Bioconjugate Chem.*, vol. 18, pp. 989-993 (2007).
International Preliminary Report on Patentability issued in International Patent Application No. PCT/US2017/039710, dated Jan. 1, 2019.
Notice of Reasons for Rejection issued in co-pending Japanese Patent Application No. 2018-568352, dated May 18, 2021.
Office Action issued in co-pending Canadian Patent Application No. 3029273, dated Aug. 15, 2023.

* cited by examiner

$^{18}$F-LABELED TRIAZOLE CONTAINING PSMA INHIBITORS

CROSS-REFERENCE TO RELATED APPLICATIONS

This application is a continuation of U.S. patent application Ser. No. 16/233,026, filed Dec. 26, 2018, which is a continuation of U.S. patent application Ser. No. 15/635,776, filed Jun. 28, 2017, which claims the benefit of and priority to U.S. Provisional Patent Application No. 62/355,430, filed Jun. 28, 2016, the entire contents of which are hereby incorporated by reference in their entirety for any and all purposes.

FIELD

The present technology is directed to compounds, compositions, and methods related to the imaging of mammalian tissues overexpressing prostate specific membrane antigen ("PSMA"), such as cancer tissue and cancer neovasculature.

SUMMARY

In an aspect, a compound according to Formula I is provided (I)

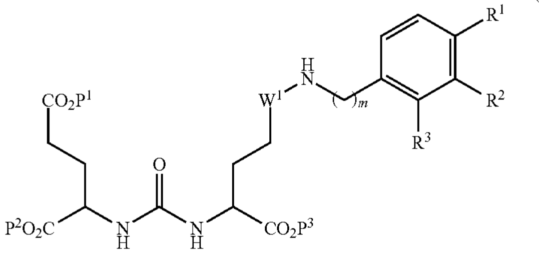

or a pharmaceutically acceptable salt thereof, where $P^1$, $P^2$, and $P^3$ are each independently H, methyl, benzyl, 4-methoxybenzyl, or tert-butyl; $W^1$ is —C(O)— or $—(CH_2)_n—NH—C(O)—$; one of $R^1$, $R^2$, and $R^3$ is

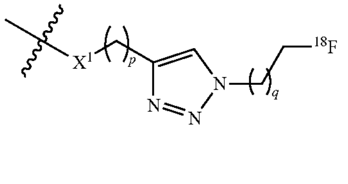

and the remaining two of $R^1$, $R^2$, and $R^3$ are each H; $X^1$ is absent, O, S, or NH; m is 0, 1, 2, or 3; n is 1 or 2; p is 0, 1, 2, or 3, provided that when p is 0 then $X^1$ is absent; and q is 1 or 2. In any embodiment herein, $P^1$, $P^2$, and $P^3$ may each independently be H or tert-butyl. In any embodiment herein, it may be that $P^1$, $P^2$, and $P^3$ are each independently H.

Similarly, a compound of Formula IV is provided (IV)

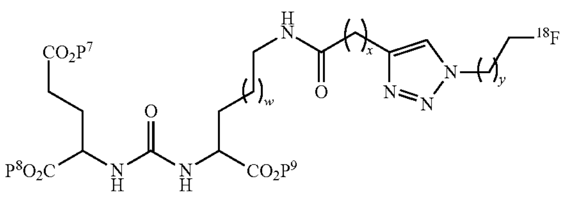

or a pharmaceutically acceptable salt thereof, where $P^7$, $P^8$, and $P^9$ are each independently H, methyl, benzyl, 4-methoxybenzyl, or tert-butyl; w is 1 or 2; x is 0, 1, 2, or 3; and y is 1 or 2. $P^7$, $P^8$, and $P^9$ are each independently be H or tert-butyl. In any embodiment herein, it may be that $P^7$, $P^8$, and $P^9$ are each independently H.

Intermediates for preparing a compound of Formula I or Formula II are also provided. Because $^{18}$F compounds are typically generated in a relatively short time period prior to use, the intermediates of the present technology provide a substantial improvement to available resources and greatly facilitate rapid and high radiochemical yield production of the targeted imaging compounds of the present technology.

A particularly useful intermediate for producing a compound of Formula I includes, but is not limited to, a compound of Formula II (II)

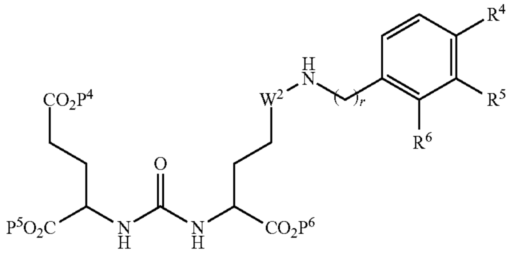

or a pharmaceutically acceptable salt thereof, where $P^4$, $P^5$, and $P^6$ are each independently H, methyl, benzyl, 4-methoxybenzyl, or tert-butyl; $W^2$ is —C(O)— or $—(CH_2)_n—NH—C(O)—$; one of $R^4$, $R^5$, and $R^6$ is

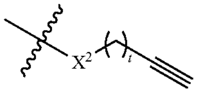

and the remaining two of $R^4$, $R^5$, and $R^6$ are each H; $X^2$ is absent, O, S, or NH; r is 0, 1, 2, or 3; s is 1 or 2; and t is 0, 1, 2, or 3, provided that when t is 0 then $X^2$ is absent.

Similarly, a particularly useful intermediate for producing a compound of Formula IV includes, but is not limited to, a compound of Formula V (V)

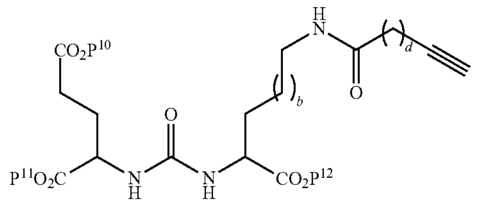

or a pharmaceutically acceptable salt thereof, where $P^{10}$, $P^{11}$, and $P^{12}$ are each independently H, methyl, benzyl, 4-methoxybenzyl, or tert-butyl; b is 1 or 2; and d is 0, 1, 2, or 3.

In a related aspect, a composition is provided that includes a compound of any embodiment of Formulas I-IV and a pharmaceutically acceptable carrier.

DETAILED DESCRIPTION

Figure 1:
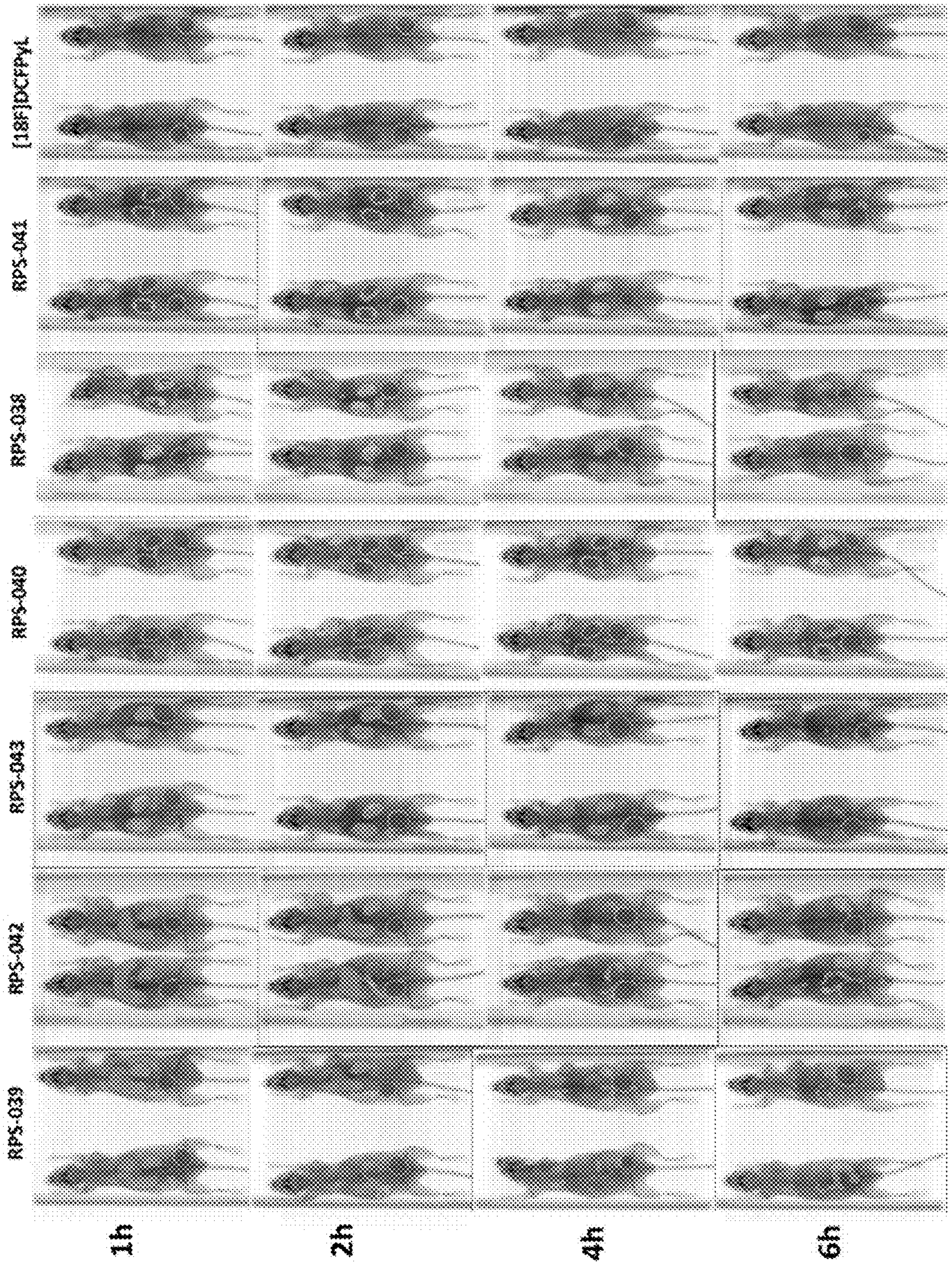
FIG. 1 provides microPET/CT images of a series of [$^{18}$F]fluorinated PSMA ligands in LNCaP xenograft-tumor bearing mice. Mice (n=2 per time point) were imaged at 1 h, 2 h, 4 h and 6 h post injection. All images are scaled to correct for decay and the highest tumor uptake image (RPS-040 of the present technology; 2 h post injection) is used as the reference for setting the intensity scale.

In various aspects, the present technology provides compounds and methods for imaging mammalian tissues overexpressing prostate specific membrane antigen ("PSMA"). The compounds provided herein can be formulated into pharmaceutical compositions and medicaments that are useful in the disclosed methods. Also provided is the use of the compounds in preparing pharmaceutical formulations and medicaments.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $^{14}$C, $^{32}$P, and $^{35}$S are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., SF5), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Alkyl groups may be substituted or unsubstituted. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Cycloalkyl groups may be substituted or unsubstituted. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. Cycloalkylalkyl groups may be substituted or unsubstituted. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups may be substituted or unsubstituted. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, $-CH{=}CH(CH_3)$, $-CH{=}C(CH_3)_2$, $-C(CH_3){=}CH_2$, $-C(CH_3){=}CH(CH_3)$, $-C(CH_2CH_3){=}CH_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups may be substituted or unsubstituted. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to $-C{\equiv}CH$, $-C{\equiv}CCH_3$, $-CH_2C{\equiv}CCH_3$, $-C{\equiv}CCH_2CH(CH_2CH_3)_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups may be substituted or unsubstituted. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. The phrase "aryl groups" includes groups containing fused rings, such as fused aromatic-aliphatic ring systems (e.g., indanyl, tetrahydronaphthyl, and the like). Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. Aralkyl groups may be substituted or unsubstituted. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. Heterocyclyl groups may be substituted or unsubstituted. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. The phrase "heteroaryl groups" includes fused ring compounds. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Alkoxy groups may be substituted or unsubstituted. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "urea" refers to —$NR^{84}$—C(O)—$NR^{85}R^{86}$ groups. $R^{84}$, $R^{85}$, and $R^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term “halogen” or “halo” as used herein refers to bromine, chlorine, fluorine, or iodine. In some embodiments, the halogen is fluorine. In other embodiments, the halogen is chlorine or bromine.

The term “hydroxyl” as used herein can refer to —OH or its ionized form, $—O^-$. A “hydroxyalkyl” group is a hydroxyl-substituted alkyl group, such as $HO—CH_2—$.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as “up to,” “at least,” “greater than,” “less than,” and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, trifluoroacetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

“Tautomers” refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

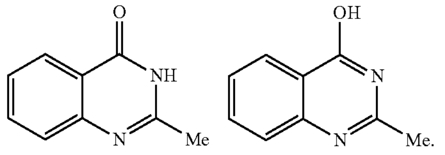

As another example, guanidines may exhibit the following isomeric forms in protic organic solution, also referred to as tautomers of each other:

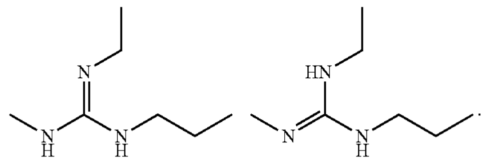

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Prostate cancer is the second most prevalent cancer among men, with more than 1.1 million diagnoses in 2012 and more than 292,000 deaths due to prostate cancer reported worldwide in 2013. The disease burden continues to grow—157,000 deaths were reported in 1990—and it is estimated that more than 180,000 men will be newly diagnosed with prostate cancer in the United States in 2016, and that more than 26,000 deaths due to the disease will be registered. When detected early and the disease is confined to the prostate gland and regional lymph nodes, the 5-year survival rate is nearly 100%, but the survival rate drops to below 30% when the disease is metastatic. Early diagnosis can significantly improve patient prognosis, while sensitive and specific localization of the disease is an important feature in the diagnosis and staging of the disease. Accurate staging is critical for appropriate patient management.

Prostate-specific membrane antigen ("PSMA"; also known as glutamate carboxypeptidase II (GCPII), N-acetyl-L-aspartyl-L-glutamate peptidase I (NAALADase I), and NAAG peptidase which is encoded by the FOLH1 (folate hydrolase 1) gene) is significantly overexpressed in prostate cancer primary tumors, cancer neo-vasculature, many metastatic lesions, and certain other diseases such as Crohn's disease and inflammatory bowel disease ("IBD"), while expression in healthy prostate and other tissue is limited. See, e.g., Silver D A, Pellicer I, Fair W R, Heston W D W, Cordon-Cardo C. Prostate-specific Membrane Antigen Expression in Normal and Malignant Human Tissues. Clin. Cancer Res. 1997, 3, 81-85 and Zhang T, Song B, Zhu W, Xu X, Gong Q Q, Morando C, Dassopoulos T, Newberry R D, Hunt S R, Li E. An Ileal Crohn's Disease Gene Signature Based on Whole Human Genome Expression Profiles of Disease Unaffected Ileal Mucosal Biopsies. PLoS One. 2012 May 14; 7(5): e37139 (doi:10.1371/journal.pone.0037139). For example, PSMA is expressed on the neo-vasculature of glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, and renal cell carcinoma. See, e.g., Wernicke A G, Kim S, Liu H, Bander N H, Pirog E C. Prostate-specific Membrane Antigen (PSMA) Expression in the Neovasculature of Gynecologic Malignancies: Implications for PSMA-targeted Therapy. Appl Immunohistochem Mol Morphol. 2016 Feb. 9 (doi: 10.1097/PAI.00000000000297); Wang H L, Wang S S, Song W H, Pan Y, Yu H P, Si T G, Liu Y, Cui X N, Guo Z. Expression of prostate-specific membrane antigen in lung cancer cells and tumor neovasculature endothelial cells and its clinical significance. PLoS One. 2015 May 15; 10(5): e0125924 (doi: 10.1371/journal.pone.0125924); Samplaski M K, Heston W, Elson P, Magi-Galluzzi C, Hansel D E. Folate hydrolase (prostate-specific membrane antigen) 1 expression in bladder cancer subtypes and associated tumor neovasculature. Mod Pathol. 2011 November; 24(11): 1521-9 (doi: 10.1038/modpathol.2011.112); Haffner M C, Kronberger I E, Ross J S, Sheehan C E, Zitt M, Muhlmann G, Ofner D, Zelger B, Ensinger C, Yang X J, Geley S, Margreiter R, Bander N H. Prostate-specific membrane antigen expression in the neovasculature of gastric and colorectal cancers. Hum Pathol. 2009 December; 40(12): 1754-61 (doi: 10.1016/j.humpath.2009.06.003); Baccala A, Sercia L, Li J, Heston W, Zhou M. Expression of prostate-specific membrane antigen in tumor-associated neovasculature of renal neoplasms. Urology. 2007 August; 70(2):385-90 (doi: 10.1016/j.urology.2007.03.025); and Chang S S, Reuter V E, Heston W D, Bander N H, Grauer L S, Gaudin P B. Five different anti-prostate-specific membrane antigen (PSMA) antibodies confirm PSMA expression in tumor-associated neovasculature. Cancer Res. 1999 Jul. 1; 59(13): 3192-8, each of which is incorporated herein by reference.

Furthermore, several other characteristics combine to make PSMA an ideal target for molecular diagnostics and therapeutics for prostate cancer: (1) it is overexpressed at all stages of the disease; (2) expression typically correlates with tumor grade, disease aggressiveness, metastasis and biochemical recurrence; (3) it is a transmembrane protein with an extracellular ligand binding domain; and (4) the bound ligand-protein complex is internalized via receptor-mediated clathrin-dependent endocytosis. The potential utility of PSMA as a target for diagnostic imaging and therapy was demonstrated with the radiolabeled monoclonal antibody J591, using In-111 or Zr-89 for imaging and Y-90 or Lu-177 for therapy, however the pharmacokinetics of the antibody make it unsuitable for diagnostic imaging with short-lived radionuclides.

Cerenkov luminescence imaging (CLI) is an imaging modality for image-guided surgery in general, and especially in regard to surgical margins in particular. CLI is based on the detection of Cerenkov photons emitted by positron emission tomography (PET) imaging agents. Cerenkov photons are emitted by a charged particle (positron or electron) when travelling through a dielectric medium at a velocity greater than the velocity of light in that medium. The Cerenkov phenomenon seems to have been first observed by Marie Curie in the late 19th century. In her biography, she describes observing a pale blue glow from the radium-containing bottles in her laboratory. The first person to systematically describe Cerenkov radiation was Pavel Cerenkov, and together with Il'ja Mikhailovic Frank and Igor Yevgenyevich Tamm who developed the theoretical framework, they won the Nobel Prize in Physics in 1958 for their contribution to the discovery of the Cerenkov effect. In the lay mind, Cerenkov radiation is known as the blue glow in the cooling water basins that surround nuclear reactors. By detecting the optical photons from PET imaging tracers, CLI combines optical and molecular imaging. CLI with PET agents has been used to image cancer in vivo, and since then, this technology has rapidly emerged in the field of biomedical imaging. See, e.g., Robertson R, Germanos M S, Li C, Mitchell G S, Cherry S R, Silva M D. Optical imaging of Cerenkov light generation from positron-emitting radiotracers. Phys Med Biol 2009, 54(16):N355-365 (doi:10.1088/0031-9155/54/16/n01) and M. R. Grootendorst M R, Cariati M, Kothari A, Tuch D S, ● Purushotham A. Cerenkov luminescence imaging (CLI) for image-guided cancer surgery. Clin Transl Imaging 2016, 4:353-366 (doi: 10.1007/s40336-016-0183-x). CLI images may be acquired by detecting the Cerenkov light from positron emitting radiotracers using ultra-high-sensitivity optical cameras such as electron-multiplying charge-coupled device (EMCCD) cameras. The CLI image can be analyzed semi-quantitatively in photon radiance. Several studies have shown a strong correlation between CLI and PET for different radiopharmaceuticals in vitro, ex vivo, and in vivo.

A number of low molecular weight, urea-based small molecules have been described as single photon emission computed tomography (SPECT) or positron emission tomography (PET) imaging agents for prostate cancer, and several of them are undergoing clinical investigation in man. Exemplary structures are provided in Scheme 1.

Scheme 1.
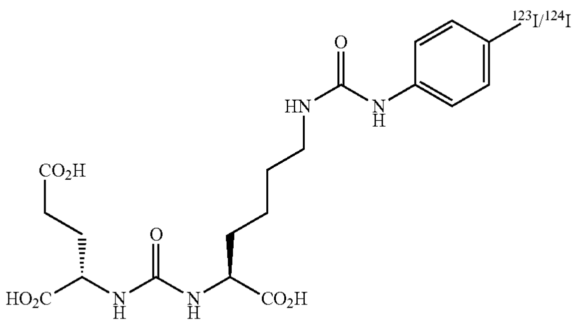
$^{123}$I/$^{124}$I-MIP-1095
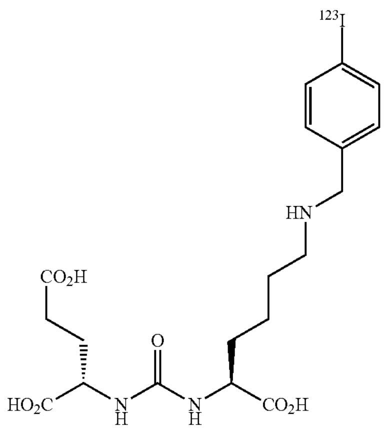
$^{123}$I-MIP-1072
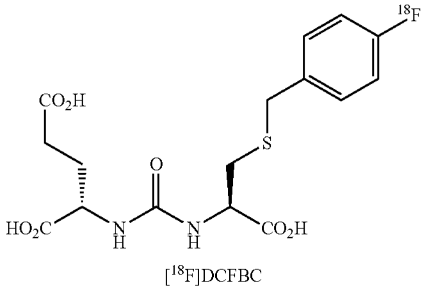
[$^{18}$F]DCFBC
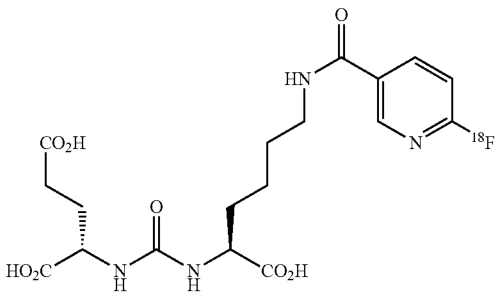
[$^{18}$F]DCFPyL
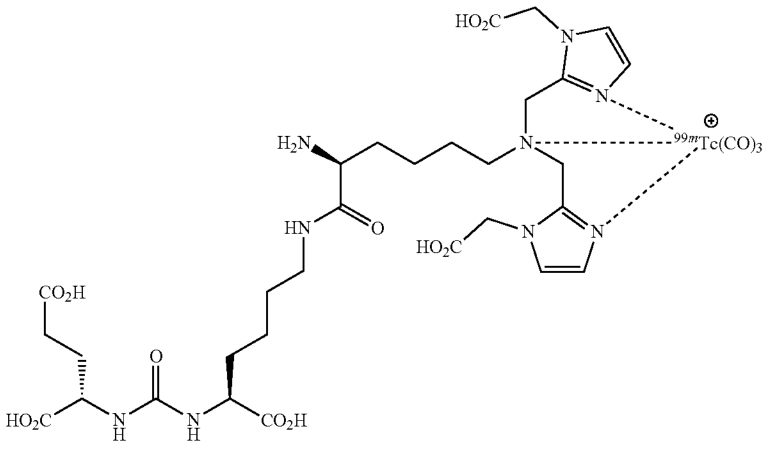
$^{99m}$Tc-MIP-1405

-continued
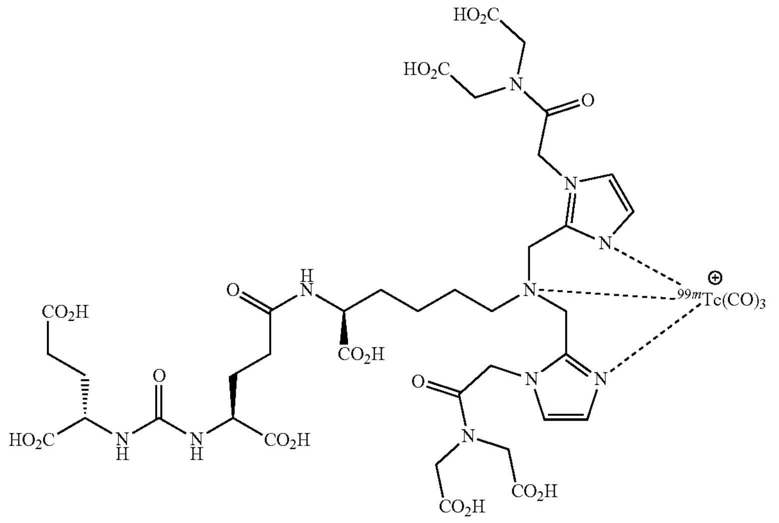
$^{99m}$Tc-MIP-1404
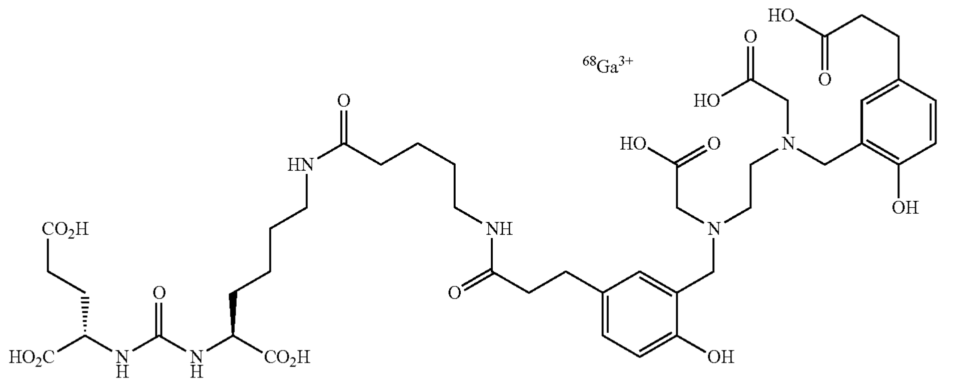
[$^{68}$Ga]Ga-PSMA-HBED-CC
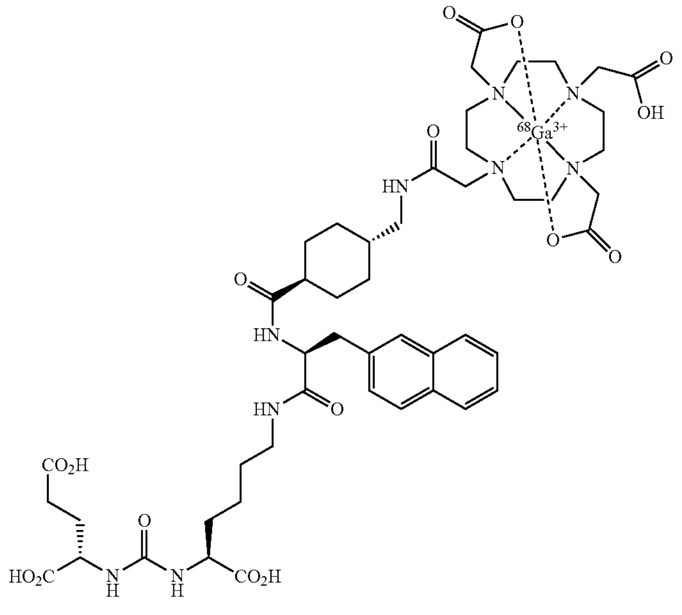
$^{68}$Ga-DKFZ-617

-continued

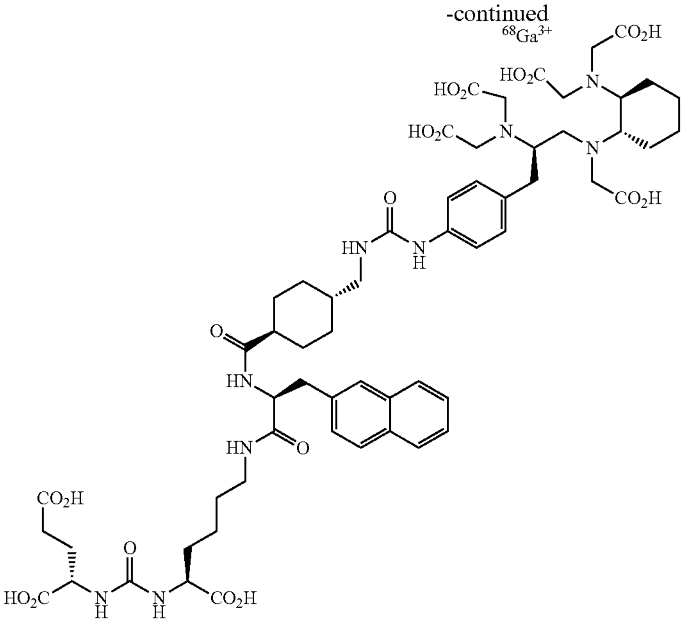

$^{68}$Ga-CHX-A"-DTPA

Currently, seven such molecules have entered or are in Phase I/II/III clinical trials in the United States and/or Europe: (i) radioiodinated MIP-1095 (I-123 for SPECT/CT and I-124 for PET/CT) and MIP-1072 (I-123 for SPECT/CT), developed by Molecular Insight Pharmaceuticals, Inc., (ii) $^{99m}$Tc-MIP-1404 and $^{99m}$Tc-MIP-1405, two further SPECT imaging agents emerging from the Molecular Insight Pharmaceuticals platform, (iii) [$^{68}$Ga]Ga-PSMA-HBED-CC (also known as [$^{68}$Ga]PSMA-11 and [$^{68}$Ga]DKFZ-PSMA-11) for PET/CT, and (iv) [$^{18}$F]DCFBC and its next generation derivative [$^{18}$F]DCFPyL for PET/CT. Newly introduced compounds to undergo first-in-man evaluation include $^{68}$Ga-DKFZ-617, developed to be a theranostic ligand and evaluated in a therapeutic context as $^{177}$Lu-DKFZ-617, and the structurally related $^{68}$Ga-CHX-A"-DTPA.

The greater sensitivity and higher spatial resolution of PET relative to SPECT has made this technique the preferred imaging platform in a number of clinical environments. Among the positron emitting isotopes currently incorporated into PSMA targeting ligands, fluorine-18 and gallium-68 are preferred to iodine-124 because of their shorter half lives, associated lower radiation dose and higher efficiency of positron emission (97% and 89% vs. 23%, respectively). Furthermore, iodine-124 scans require complex reconstruction algorithms to minimize the signal-to-noise ratio, which, in combination with the long half-life of iodine-124 ($t_{1/2}$=4.18 d) and the undesired emission of beta particles, is often a poor match for the pharmacokinetics of small molecules. In addition, gallium-68 is currently produced from a $^{68}$Ge/$^{68}$Ga generator, enabling its use in single batch syntheses in radiopharmacies independent of access to a cyclotron, and chelation of gallium-68 is both clean and rapid under conditions that are compatible with most small molecule and peptides. These considerations have contributed to the emergence of [$^{68}$Ga]Ga-PSMA-HBED-CC as the most widely used PSMA PET radiotracer currently in clinical development.

Fluorine-18 presents a number of practical advantages compared to gallium-68, including: (i) a longer half-life ($t_{1/2}$($^{18}$F)=109.8 min vs. $t_{1/2}$($^{68}$Ga)=67.7 min), which permits multiple step radiosyntheses and allows a longer time for background signal to clear before imaging is performed, (ii) large scale cyclotron production that allows multiple patient doses to be produced from a single synthesis, and (iii) chemical characteristics, such as a similar atomic radius to hydrogen, that allow diverse types of ligand to be prepared. On this basis, the development of PSMA-targeting ligands labeled with fluorine-18 has emerged recently as a goal of great interest. [$^{18}$F]DCFBC is based on a Glu-urea-Cys pharmacophore modified with a 4-[$^{18}$F]fluorobenzyl group, and was reported to show good uptake in PSMA$^{+}$ xenograft tumors. In man, however, it has shown limited clearance from soft tissue, resulting in a decreased tumor-to-background ratio and poor visualization of small lesions. To address the slow clearance, the second generation [$^{18}$F] fluoropyridine-modified Glu-urea-Lys analogue [$^{18}$F] DCFPyL was developed. Despite more promising pharmacokinetics, fast tumor washout is evident as early as 1 h post injection and accumulation of radioactivity in evacuated bladders is considerable. In addition, [$^{18}$F]DCFPyL suffers from poor radiochemical yields (in the range 5-12% decay corrected, although recently an improved synthesis by direct fluorination has been reported to increase yield to greater than 20%).

The present technology addresses the aforementioned challenges in the development of fluorine-18-PSMA ligands of high specificity and affinity. Compounds of the present technology exhibit substantial tumor uptake in nude mice bearing LNCaP xenografts using pPET/CT. For example, two compounds of the present technology, RPS-040 and RPS-041, show excellent PSMA imaging characteristics based on their high specificity for PSMA, high tumor uptake and prolonged tumor retention, rapid clearance from non-target tissues and resulting high tumor-to-background ratios. The compounds of the present technology also show superior pharmacokinetics when compared to [$^{68}$Ga]Ga-PSMA-HBED-CC in mice.

Furthermore, the present technology provides advanced intermediates that allow for facile and rapid production of the $^{18}F$-bearing compounds of the present technology, allowing for relatively easy production of the compounds of the present technology prior to use.

Thus, in an aspect, a compound according to Formula I is provided (I)

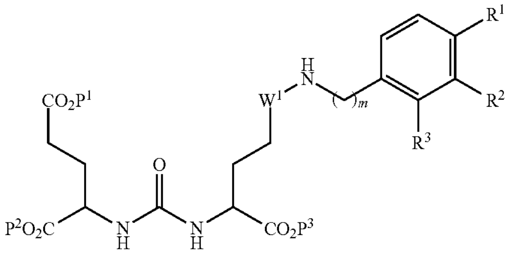

or a pharmaceutically acceptable salt thereof, where $P^1$, $P^2$, and $P^3$ are each independently H, methyl, benzyl, 4-methoxybenzyl, or tert-butyl; $W^1$ is —C(O)— or —$(CH_2)_n$—NH—C(O)—; one of $R^1$, $R^2$, and $R^3$ is

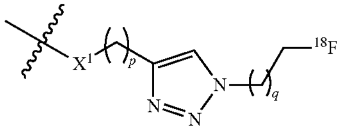

and the remaining two of $R^1$, $R^2$, and $R^3$ are each H; $X^1$ is absent, O, S, or NH; m is 0, 1, 2, or 3; n is 1 or 2; p is 0, 1, 2, or 3, provided that when p is 0 then $X^1$ is absent; and q is 1 or 2. In any embodiment herein, $P^1$, $P^2$, and $P^3$ may each independently be H or tert-butyl. In any embodiment herein, it may be that $P^1$, $P^2$, and $P^3$ are each independently H.

Similarly, a compound of Formula IV is provided (IV)

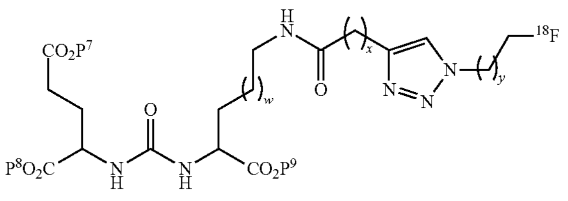

or a pharmaceutically acceptable salt thereof, where $P^7$, $P^8$, and $P^9$ are each independently H, methyl, benzyl, 4-methoxybenzyl, or tert-butyl; w is 1 or 2; x is 0, 1, 2, or 3; and y is 1 or 2. $P^7$, $P^8$, and $P^9$ are each independently be H or tert-butyl. In any embodiment herein, it may be that $P^7$, $P^8$, and $P^9$ are each independently H.

Intermediates for preparing a compound of Formula I or Formula IV are also provided. Because $^{18}F$ compounds are typically generated in a relatively short time period prior to use, the intermediates of the present technology provide a substantial improvement to available resources and greatly facilitate rapid production of the targeted imaging compounds of the present technology with high radiochemical yield.

A particularly useful intermediate for producing a compound of Formula I includes, but is not limited to, a compound of Formula II (II)

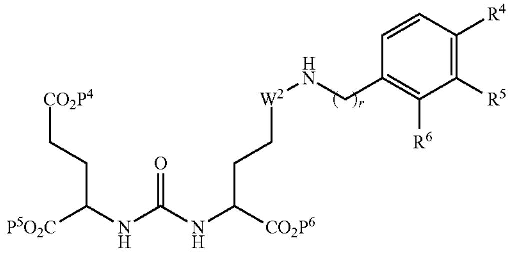

or a pharmaceutically acceptable salt thereof, where $P^4$, $P^5$, and $P^6$ are each independently H, methyl, benzyl, 4-methoxybenzyl, or tert-butyl; $W^2$ is —C(O)— or —$(CH_2)_n$—NH—C(O)—; one of $R^4$, $R^5$, and $R^6$ is

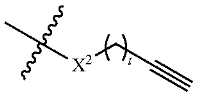

and the remaining two of $R^4$, $R^5$, and $R^6$ are each H; $X^2$ is absent, O, S, or NH; r is 0, 1, 2, or 3; s is 1 or 2; and t is 0, 1, 2, or 3, provided that when t is 0 then $X^2$ is absent.

Similarly, a particularly useful intermediate for producing a compound of Formula IV includes, but is not limited to, a compound of Formula V (V)

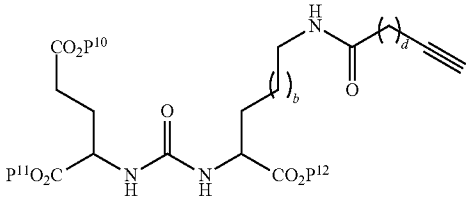

or a pharmaceutically acceptable salt thereof, where $P^{10}$, $P^{11}$, and $P^{12}$ are each independently H, methyl, benzyl, 4-methoxybenzyl, or tert-butyl; b is 1 or 2; and d is 0, 1, 2, or 3.

In a related aspect, a method of forming a compound of any embodiment of Formula I is provide. The method includes contacting in the presence of a solvent a compound of Formula II, a copper salt, and an azide of Formula III (III)

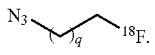

The copper salt may be a copper (I) salt (such as copper (I) iodide), a copper (II) salt (such as copper (II) sulfate), or a mixture thereof. The solvent may be a protic solvent, and aprotic solvent, or a mixture thereof. Protic solvents as used herein include, but are not limited to, alcohols (e.g., methanol ($CH_3OH$), ethanol (EtOH), isopropanol (iPrOH), trifluoroethanol (TFE), butanol (BuOH), ethylene glycol, propylene glycol), carboxylic acids (e.g., formic acid, acetic acid, propanoic acid, butanoic acid, pentanoic acid, lauric acid, stearic acid, deoxycholic acid, glutamic acid, glucuronic acid), ammonia ($NH_3$), a primary amino compound (e.g., methyl amine, ethyl amine, propyl amine), a secondary amino compound (e.g., dimethyl amine, diethyl amine, di(n-propyl) amine), water, or a mixture of any two or more thereof. Polar aprotic solvents as used herein include, but are not limited to, ethers (e.g., tetrahydrofuran (THF), 2-methyltetrahydrofuran (2Me-THF), dimethoxyethane (DME), dioxane), esters (e.g., ethyl acetate, isopropyl acetate), ketones (e.g., acetone, methylethyl ketone, methyl isobutyl ketone), carbonates (e.g., ethylene carbonate, propylene carbonate, trimethylene carbonate), amides (e.g., dimethylformamide (DMF), dimethylacetamide (DMA)), nitriles (e.g., acetonitrile ($CH_3CN$), propionitrile ($CH_3CH_2CN$), benzonitrile (PhCN)), sulfoxides (e.g., dimethyl sulfoxide, also referred to as "DMSO"), sulfones (e.g., sulfolane), or a mixture of any two or more thereof. For example, the solvent may include DMF and DMSO.

In a similar aspect, a method of forming a compound of any embodiment of Formula IV is provide. The method includes contacting in the presence of a solvent a compound of Formula V, a copper salt, and an azide of Formula VI (VI)

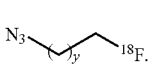

The copper salt may be a copper (I) salt (such as copper (I) iodide), a copper (II) salt (such as copper (II) sulfate), or a mixture thereof. The solvent may be a protic solvent, and aprotic solvent, or a mixture thereof. Such protic solvents, aprotic solvents, and mixtures thereof are discussed supra. In any embodiment of the method, the solvent may include DMF and DMSO.

In an aspect of the present technology, a composition is provided that includes any one of the aspects and embodiments of compounds of Formulas I, II, IV & V and a pharmaceutically acceptable carrier. As used herein, a "pharmaceutically acceptable carrier" includes carriers and/or excipients. In a related aspect, a pharmaceutical composition is provided, the pharmaceutical composition including an effective amount of the compound of any one of the aspects and embodiments of compounds of Formulas I & IV for imaging a condition; and where the condition includes a mammalian tissue overexpressing PSMA, such as a cancer expressing PSMA (including cancer tissues, cancer related neo-vasculature, or a combination thereof), Crohn's disease, or IBD. In a further related aspect, an imaging method is provided that includes administering a compound of any one of the aspects and embodiments of compounds of Formulas I & IV (e.g., such as administering an effective amount) or administering a pharmaceutical composition comprising an effective amount of a compound of any one of the aspects and embodiments of compounds of Formulas I & IV to a subject and, subsequent to the administering, detecting positron emission, detecting gamma rays from positron emission and annihilation (such as by positron emission tomography), and/or detecting Cerenkov radiation due to positron emission (such as by Cerenkov luminescence imaging). In any embodiment of the imaging method, the subject may be suspected of suffering from a condition that includes a mammalian tissue overexpressing PSMA, such as a cancer expressing PSMA (including cancer tissues, cancer related neo-vasculature, or a combination thereof), Crohn's disease, or IBD. The cancer of the pharmaceutical composition and/or the method may include one or more of glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, and prostate cancer. The prostate cancer may include castration resistant prostate cancer. The detecting step may occur during a surgical procedure on a subject, e.g., to remove a mammalian tissue overexpressing PSMA. The detecting step may include use of a handheld device to perform the detecting step. For example, Cerenkov luminescence images may be acquired by detecting the Cerenkov light using ultra-high-sensitivity optical cameras such as electron-multiplying charge-coupled device (EMCCD) cameras.

"Effective amount" refers to the amount of a compound or composition required to produce a desired effect, such as a quantity of a compound of the present technology necessary to be detected by the detection method chosen. For example, an effective amount of a compound of the present technology includes an amount sufficient to enable detection of binding of the compound to a target of interest including, but not limited to, one or more of glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, and prostate cancer (such as castration resistant prostate cancer). Another example of an effective amount includes amounts or dosages that are capable of providing a detectable gamma ray emission from positron emission and annihilation (above background) in a subject with a tissue overexpressing PSMA, such as, for example, statistically significant emission above background. Another example of an effective amount includes amounts or dosages that are capable of providing a detectable Cerenkov radiation emission due to positron emission above background) in a subject with a tissue overexpressing PSMA, such as, for example, statistically significant emission above background. As used herein, a "subject" or "patient" is a mammal, such as a cat, dog, rodent or primate. Typically the subject is a human, and, preferably, a human suffering from or suspected of suffering from a condition that includes a mammalian tissue overexpressing PSMA, such as a cancer expressing PSMA (including cancer tissues, cancer related neo-vasculature, or a combination thereof), Crohn's disease, or IBD. Such a condition may include one or more of glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, and prostate cancer (such as castration resistant prostate cancer). The term "subject" and "patient" may be used interchangeably.

The instant present technology provides pharmaceutical compositions and medicaments comprising any of the compounds disclosed herein (e.g., compounds of Formulas I, II, IV, and V) and a pharmaceutically acceptable carrier or one or more excipients or fillers (collectively, such carriers, excipients, fillers, etc., will be referred to as "pharmaceutically acceptable carriers" unless a more specific term is used). The compositions may be used in the methods and imagings described herein. Such compositions and medicaments include an effective amount of any compound as described herein, including but not limited to a compound of Formulas I & IV, for imaging one or more of the herein-described conditions. The pharmaceutical composition may be packaged in unit dosage form. For example, the unit dosage form is effective in imaging a mammalian tissue overexpressing PSMA, such as a cancer expressing PSMA (including cancer tissues, cancer related neo-vasculature, or a combination thereof), Crohn's disease, or IBD, when administered to a subject. The cancer expressing PSMA may include one or more of glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, and prostate cancer.

The pharmaceutical compositions and medicaments may be prepared by mixing one or more compounds of the present technology, pharmaceutically acceptable salts thereof, stereoisomers thereof, tautomers thereof, or solvates thereof, with pharmaceutically acceptable carriers, excipients, binders, diluents or the like to image disorders associated with a mammalian tissue overexpressing PSMA, such as a cancer expressing PSMA (including cancer tissues, cancer related neo-vasculature, or a combination thereof), Crohn's disease, or IBD, when administered to a subject. The cancer expressing PSMA may include one or more of glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, and prostate cancer. The compounds and compositions described herein may be used to prepare formulations and medicaments for imaging a variety of disorders associated with a mammalian tissue overexpressing PSMA. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or antioxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. An isotonic solution will be understood as isotonic with the subject. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until, for example, statistically significant resolution (via, e.g., positron emission tomography or Cerenkov luminescence imaging) of a mammalian tissue that overexpresses PSMA is achieved. The compounds of the present technology may be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being imaged and the pharmacological activity of the compound being used. The determination of optimum dosages for a particular patient is well known to those skilled in the art. Various assays and model systems can be readily employed to determine the effectiveness of a compound according to the present technology.

The compounds of the present technology can also be administered to a patient along with other conventional imaging agents that may be useful in the imaging of a mammalian tissue overexpressing PSMA. Such mammalian tissues include, but are not limited to, a cancer expressing PSMA (including cancer tissues, cancer related neo-vasculature, or a combination thereof), Crohn's disease, or IBD, when administered to a subject. The cancer expressing PSMA may include one or more of glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, and prostate cancer. Thus, a pharmaceutical composition of the present technology may further include an imaging agent different than the compounds of Formulas I & IV. The administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration. The methods of the present technology may also include administering, either sequentially or in combination with one or more compounds of the present technology, a conventional imaging agent in an amount that can potentially or synergistically be effective for the imaging of a mammalian tissue overexpressing PSMA.

In an aspect, a compound of the present technology is administered to a patient in an amount or dosage suitable for imaging. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1\times10^{-4}$ g/kg to 1 g/kg, preferably, $1\times10^{-3}$ g/kg to 1.0 g/kg. Dosage of a compound of the present technology can also vary from 0.01 mg/kg to 100 mg/kg or, preferably, from 0.1 mg/kg to 10 mg/kg.

A compound of the present technology can also be modified, for example, by the covalent attachment of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkane glycol (e.g., polyethylene glycol (PEG), polypropylene glycol (PPG)), carbohydrate polymer, amino acid polymer or polyvinyl pyrolidone and a fatty acid or fatty acid ester group, each of which can independently comprise from about eight to about seventy carbon atoms. Conjugates for use with a compound of the present technology can also serve as linkers to, for example, any suitable substituents or groups, radiolabels (marker or tags), halogens, proteins, enzymes, polypeptides, other therapeutic agents (for example, a pharmaceutical or drug), nucleosides, dyes, oligonucleotides, lipids, phospholipids and/or liposomes. In one aspect, conjugates can include polyethylene amine (PEI), polyglycine, hybrids of PEI and polyglycine, polyethylene glycol (PEG) or methoxypolyethylene glycol (mPEG). A conjugate can also link a compound of the present technology to, for example, a label (fluorescent or luminescent) or marker (radionuclide, radioisotope and/or isotope) to comprise a probe of the present technology. Conjugates for use with a compound of the present technology can, in one aspect, improve in vivo half-life. Other exemplary conjugates for use with a compound of the present technology as well as applications thereof and related techniques include those generally described by U.S. Pat. No. 5,672,662, which is hereby incorporated by reference herein.

The terms "associated" and/or "binding" can mean a chemical or physical interaction, for example, between a compound of the present technology and a target of interest. Examples of associations or interactions include covalent bonds, ionic bonds, hydrophilic-hydrophilic interactions, hydrophobic-hydrophobic interactions and complexes. Associated can also refer generally to "binding" or "affinity" as each can be used to describe various chemical or physical interactions. Measuring binding or affinity is also routine to those skilled in the art. For example, compounds of the present technology can bind to or interact with a target of interest or precursors, portions, fragments and peptides thereof and/or their deposits.

The examples herein are provided to illustrate advantages of the present technology and to further assist a person of ordinary skill in the art with preparing or using the compounds of the present technology or salts, pharmaceutical compositions, derivatives, solvates, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

General Synthetic and Analytical Details:

All solvents were purchased from Sigma Aldrich and were of reagent grade quality unless otherwise indicated. Solvents were dried either by distillation over an activated stainless steel column (Pure Process Technology, LLC) column or by drying over activated molecular sieves. Reagents were purchased from Sigma Aldrich, Alfa Aesar, Combi Blocks, ChemBridge and Enamine, and were of reagent grade with the exception of 3-(prop-2-yn-1-yloxy) aniline (Enamine), which was 80-85% pure by HPLC.

All reactions were carried out in dried glassware. Purifications were performed using silica chromatography on VWR® High Purity Silica Gel 60 Å. Preparative HPLC was performed using an XBridge™ Prep C18 5 μm OBD™ 19×100 mm column (Waters) on a dual pump Agilent ProStar HPLC fitted with an Agilent ProStar 325 Dual Wavelength UV-Vis Detector. UV absorption was monitored at 220 nm and 280 nm. A binary solvent system was used, with solvent A comprising $H_2O$+0.01% TFA and solvent B consisting of 90% v/v $MeCN/H_2O$+0.01% TFA. Purification was achieved using the following gradient HPLC method: 0% B 0-1 min., 0-100% B 1-28 mins., 100-0% B 28-30 mins.

Final products were identified and characterized using thin layer chromatography, analytical HPLC, mass spectroscopy and NMR spectroscopy. Analytical HPLC was performed using an XSelect™ CSH™ C18 5 μm 4.6×50 mm column (Waters). Mass determinations were performed by LCMS analysis using a Waters ACQUITY UPLC® coupled to a Waters SQ Detector 2. NMR analyses were performed using a Bruker Avance III 500 MHz spectrometer. Spectra are reported as ppm and are referenced to the solvent resonances in in DMSO-d6 or chloroform-d (Sigma Aldrich). The purity of all compounds evaluated in the biological assay was >95% purity as judged by LC-MS and 1H NMR.

Representative Synthesis of Intermediates of the Present Technology.

Representative synthetic procedures (Routes A & B) are provided below in Scheme 2 for generating exemplary intermediates of the present technology.

Scheme 2.

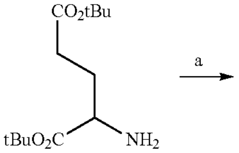

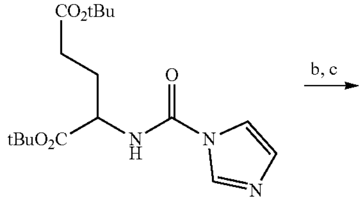

(17)

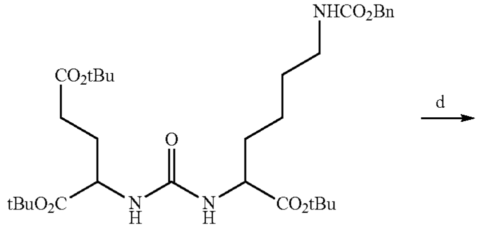

(18)

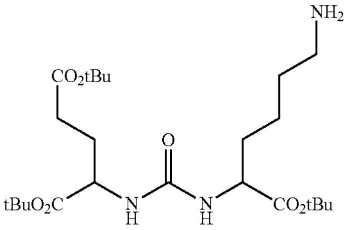

(1)

Route A (1)

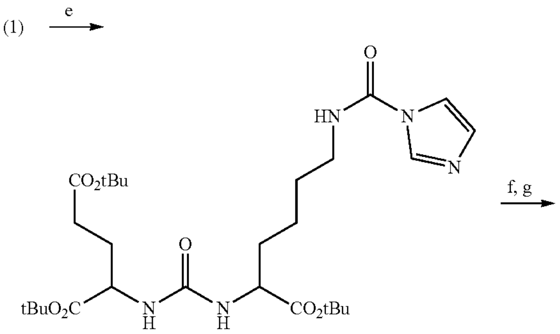

(2)

-continued

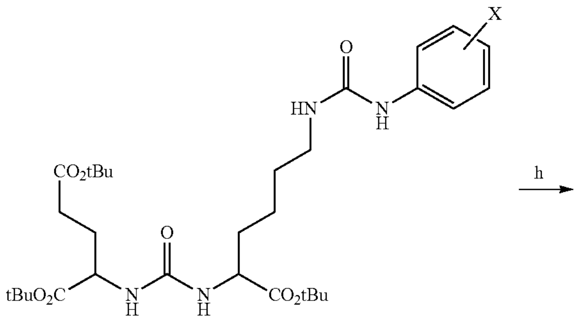

(3): X = -2-OCH$_2$CCH
(4): X = -3-CCH
(5): X = -4-OCH$_2$CCH

-continued

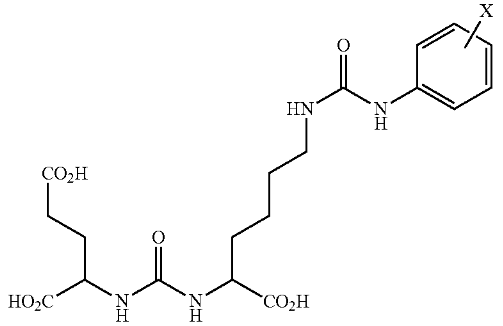

(10): X = -2-CCH
(11): X = -3-OCH$_2$CCH
(12): X = -4-CCH a. DMAP, CDI, NEt$_3$; b. MeOTf, NEt$_3$, 0° C.; c. H$_2$N-Lys(Cbz)-OtBu; d. H$_2$, Pd/C; e. DMAP, CDI, NEt$_3$; f. MeOTf, NEt$_3$, 0° C.; g. 2- or 4-(2-propyn-1-yloxy)aniline or 3-ethynylaniline, rt; h. TFA/CH$_2$Cl$_2$; i. TFA/CH$_2$Cl$_2$; j. triphosgene, NEt$_3$, reflux; k. NEt$_3$, rt.

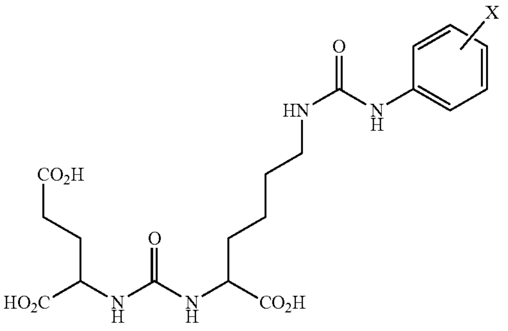

(6): X = -2-OCH$_2$CCH
(7): X = -3-CCH
(8): X = -4-OCH$_2$CCH

Route B

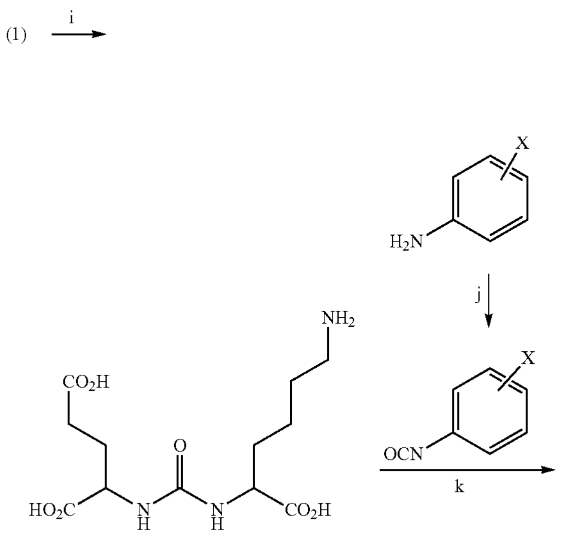

(9)

The synthesis of exemplary intermediates via Route A and Route B are provided below.

Di-tert-butyl (1H-imidazole-1-carbonyl)-L-glutamate (17). The hydrochloride salt of L-H-Glu(OtBu)-OtBu (1.25 g, 4.23 mmol) was dissolved in $CH_2Cl_2$ (30 mL) with a catalytic amount of N,N'-dimethylaminopyridine (50 mg), and the solution was cooled to 0° C. and stirred under Ar. Triethylamine (4.5 mL) was added followed by 1,1'-carbonyldiimidazole (754 mg, 4.65 mmol), and the resulting mixture was stirred overnight with warming to room temperature. The reaction was then diluted with $CH_2Cl_2$ and washed successively with $H_2O$ and saturated NaCl solution. The organic layer was dried over $MgSO_4$, filtered and concentrated under reduced pressure to give an oil that solidified upon standing. The crude product was purified by silica chromatography (0-100% MeOH in EtOAc) to give the product, di-tert-butyl (1H-imidazole-1-carbonyl)-L-glutamate (17), as a transparent oil (1.00 g, 61% yield). $^1$H NMR (500 MHz, $CDCl_3$) δ 8.18 (s, 1H), 7.48 (d, 1H, J=6.2 Hz), 7.42 (s, 1H), 7.10 (s, 1H), 4.45 (m, 1H), 2.44 (m, 2H), 2.18 (m, 2H), 1.50 (s, 9H), 1.46 (s, 9H).

Tri-tert-butyl (9S,13S)-3,11-dioxo-1-phenyl-2-oxa-4,10,12-triazapentadecane-9,13,15-tricarboxylate (18). A solution of di-tert-butyl (1H-imidazole-1-carbonyl)-L-glutamate (17) (572 mg, 1.48 mmol) in dichloroethane (6 mL) was cooled to 0° C. and stirred under Ar. A solution of trimethylamine (0.42 mL, 3.0 mmol) in dichloroethane (1 mL) was added followed by a solution of methyl triflate (160 μL, 1.5 mmol) in dichloroethane. The reaction was stirred for 60 min, warming to room temperature. Then a solution of L-H-Lys(Cbz)-OtBu.HCl (552 mg, 1.48 mmol) in dichloroethane (10 mL) was added, and the reaction was stirred for 6 h at 50° C. under Ar. The mixture was then cooled to room temperature and concentrated under reduced pressure to give an oil. The oil was purified by silica chromatography (20% EtOAC in hexanes to 50% EtOAc in hexanes) to give the product, tri-tert-butyl (9S,13S)-3,11-dioxo-1-phenyl-2-oxa-4,10,12-triazapentadecane-9,13,15-tricarboxylate (18), as a transparent oil (678 mg, 74% yield).

Di-tert-butyl (((S)-6-amino-1-(tert-butyloxy)-1-oxohexan-2-yl)carbamoyl)-L-glutamate (1). Activated palladium on carbon (0.1 eq) was suspended in a solution of tri-tert-butyl (9S,13S)-3,11-dioxo-1-phenyl-2-oxa-4,10,12-triazapentadecane-9,13,15-tricarboxylate (18) (500 mg) in EtOH (15 mL). The suspension was stirred overnight at room temperature under $H_2$ atmosphere. The mixture was then filtered through celite, and the filtrate was concentrated under reduced pressure to give the product, di-tert-butyl (((S)-6-amino-1-(tert-butyoxy)-1-oxohexan-2-yl)carbamoyl)-L-glutamate (1) as a viscous oil (360 mg, 92% yield).

Route A Synthesis

Di-tert-butyl (((S)-1-(tert-butoxy)-6-(1H-imidazole-1-carboxamido)-1-oxohexan-2-yl)carbamoyl)-L-glutamate (2). Compound 1 (1.46 g, 3.0 mmol) was dissolved in dichloroethane (10 mL) with triethylamine (0.84 mL, 6.0 mmol) and a catalytic amount of N,N'-dimethylaminopyridine (15 mg) and stirred at room temperature under Ar. After 5 min, a suspension of 1,1'-carbonyldiimidazole (486 mg, 3.3 mmol) in dichloroethane (2 mL) was added, and the reaction was stirred overnight under Ar. The solution was then washed successively with 1% v/v AcOH in $H_2O$ and saturated NaCl solution. The organic layer was dried over $MgSO_4$, filtered and concentrated under reduced pressure to give a yellow oil. The oil was purified by silica chromatography (50% EtOAc in hexanes to 10% MeOH in EtOAc) to give the product, di-tert-butyl (((S)-1-(tert-butoxy)-6-(1H-imidazole-1-carboxamido)-1-oxohexan-2-yl)carbamoyl)-L-glutamate (2), as an off white powder (60% yield). $^1H$ NMR (500 MHz, $CDCl_3$) δ 8.34 (s, 1H), 7.94 (br s, 1H), 7.69 (s, 1H), 7.05 (s, 1H), 5.95 (d, 1H, J=7.8 Hz), 5.58 (d, 1H, J=7.6 Hz), 4.21 (m, 1H), 4.16 (m, 1H), 3.53 (m, 1H), 3.28 (m, 1H), 2.30 (m, 2H), 2.05 (m, 1H), 1.83 (m, 1H), 1.79 (m, 1H), 1.72 (m, 1H), 1.50 (m, 2H), 1.43 (s, 18H), 1.38 (s, 9H), 1.32 (m, 2H). ESI(+)=582.5 $(M+H)^+$. Calculated mass: 581.34.

Di-tert-butyl (((S)-1-(tert-butoxy)-1-oxo-6-(3-(2-prop-2-yn-1-yloxy)phenyl)ureido)hexan-2-yl)carbamoyl)-L-glutamate (3). A solution of di-tert-butyl (((S)-1-(tert-butoxy)-6-(1H-imidazole-1-carboxamido)-1-oxohexan-2-yl)carbamoyl)-L-glutamate (2) (182 mg, 0.30 mmol) in dichloroethane (4 mL) was cooled to 0° C. and stirred under Ar. A solution of triethylamine (87 μL, 0.63 mmol) in dichloroethane (1 mL) was added followed by a solution of methyl triflate (34 uL, 0.31 mmol) in dichloroethane (1 mL). The reaction was stirred for 60 min, warming to room temperature. Then 2 mL of the reaction mixture was transferred under Ar to a round-bottom flask containing a solution of 2-(2-propyn-1-yloxy)aniline (15 mg, 0.10 mmol) in dichloroethane (1 mL). The resulting mixture was stirred at room temperature for 16 h under Ar. The mixture was then cooled to room temperature and concentrated under reduced pressure to give an oil. The oil was purified by reverse phase prep HPLC (12 mL/min, 0% B to 100% B over 30 min followed by 5 min at 100% B; X=220 nm, 254 nm). The peak containing the product was lyophilized and the product, di-tert-butyl (((S)-1-(tert-butoxy)-1-oxo-6-(3-(2-prop-2-yn-1-yloxy)phenyl)ureido)hexan-2-yl)carbamoyl)-L-glutamate (3), was isolated as a white powder (28 mg, 45% yield). $^1H$ NMR (500 MHz, $CDCl_3$) δ 8.20 (d, 1H, J=7.8 Hz), 7.45 (br s, 1H), 6.97 (m, 1H), 6.84 (m, 2H), 6.71 (m, 2H), 6.00 (br s, 1H), 5.69 (br s, 1H), 5.50 (d, 1H, J=7.0 Hz), 4.67 (dd, 2H, $J_1$=7.2 Hz, $J_2$=2.4 Hz), 4.36 (m, 1H), 4.21 (m, 1H), 3.12 (m, 2H), 2.54 (t, 1H, J=2.4 Hz), 2.33 (m, 2H), 2.03 (m, 1H), 1.87 (m, 1H), 1.75 (m, 1H), 1.54-1.38 (m, 5H), 1.41 (s, 18H), 1.37 (s, 9H). ESI(+)=661.5 $(M+H)^+$. Calculated mass: 660.37.

Di-tert-butyl (((S)-1-(tert-butoxy)-6-(3-(2-ethynylphenyl)ureido)-1-oxohexan-2-yl)carbamoyl)-L-glutamate (4). The compound was synthesized by the same method from 3-ethynyl aniline (1.1 eq) and urea (2) (1.0 eq) and isolated as an orange semi-solid (33%). $^1H$ NMR (500 MHz, $CDCl_3$) δ 7.90 (s, 1H), 7.58 (t, 1H, J=1.7 Hz), 7.51 (dd, 1H, $J_1$=8.2 Hz, $J_2$=1.3 Hz), 7.18 (t, 1H, J=7.9 Hz), 7.05 (d, 1H, J=7.7 Hz), 6.38 (d, 1H, J=7.9 Hz), 6.28 (br s, 1H), 5.77 (d, 1H, J=6.9 Hz), 4.32 (m, 1H), 4.02 (m, 1H), 3.53 (m, 1H), 3.05 (m, 1H), 3.00 (s, 1H), 2.39 (m, 2H), 2.07 (m, 1H), 1.88 (m, 1H), 1.74 (m, 1H), 1.62 (m, 1H), 1.49-1.37 (m, 4H), 1.41 (s, 18H), 1.37 (s, 9H). ESI(+)=631.5 $(M+H)^+$. Calculated mass: 630.36.

Di-tert-butyl (((S)-1-(tert-butoxy)-1-oxo-6-(3-(4-prop-2-yn-1-yloxy)phenyl)ureido)hexan-2-yl)carbamoyl)-L-glutamate (5). The compound was synthesized by the same method from [4-(2-propyn-1-yloxy)phenyl]amine hydrochloride (1.1 eq) and urea (2) (1.0 eq) and isolated as a light brown oil (46%). $^1H$ NMR (500 MHz, $CDCl_3$) δ 7.60 (s, 1H), 7.33 (d, 2H, J=9.0 Hz), 6.86 (d, 2H, J=9.0 Hz), 6.24 (d, 1H, J=7.8 Hz), 6.05 (br s, 1H), 5.71 (d, 1H, J=7.0 Hz), 4.61 (d, 2H, J=2.3 Hz), 4.30 (m, 1H), 4.03 (m, 1H), 3.45 (m, 1H), 3.05 (m, 1H), 2.47 (t, 1H, J=2.3 Hz), 2.31 (m, 2H), 2.06 (m, 1H), 1.83 (m, 1H), 1.75 (m, 1H), 1.48 (m, 3H), 1.41 (s, 9H), 1.39 (s, 9H), 1.37 (s, 9H), 1.31 (m, 2H). ESI(+)=661.4 $(M+H)^+$. Calculated mass: 660.37.

(((S)-1-Carboxy-5-(3-(2-(prop-2-yn-1-yloxy)phenyl)ureido)pentyl)carbamoyl)-L-glutamic acid (6). Di-tert-butyl (((S)-1-(tert-butoxy)-1-oxo-6-(3-(2-prop-2-yn-1-yloxy)phenyl)ureido)hexan-2-yl)carbamoyl)-L-glutamate (3) (4.2 mg, 6.4 μmol) was dissolved in $CH_2Cl_2$ (0.5 mL). Trifluoroacetic acid (0.5 mL) was added, and the mixture was stirred overnight at room temperature. The volatile solvents were removed under a stream of N2, and the resulting crude residue was lyophilized to give the product, (((S)-1-carboxy-5-(3-(2-(prop-2-yn-1-yloxy)phenyl)ureido)pentyl)carbamoyl)-L-glutamic acid (6) as a white powder (3.1 mg, 98% yield). $^1H$ NMR (500 MHz, DMSO-d6) δ 8.10 (m, 1H), 7.83 (s, 1H), 7.03 (m, 1H), 6.90 (br s, 1H), 6.86 (m, 2H), 6.33 (d, 1H, J=12.5 Hz), 6.31 (d, 1H, J=12.5 Hz), 4.86 (d, 2H, J=2.3 Hz), 4.10 (m, 2H), 3.60 (t, 1H, J=2.3 Hz), 3.06 (m, 2H), 2.24 (m, 2H), 1.93 (m, 1H), 1.69 (m, 2H), 1.56 (m, 1H), 1.42 (m, 2H), 1.32 (m, 2H). ESI(+)=493.3 $(M+H)^+$. Calculated mass: 492.19.

(((S)-1-carboxy-5-(3-(3-ethynylphenyl)ureido)pentyl)carbamoyl)-L-glutamic acid (7). Alkyne (4) was deprotected by the same method and the title compound was isolated as a white powder (61%). $^1H$ NMR (500 MHz, DMSO-d6) δ 8.42 (s, 1H), 7.11 (m, 2H), 6.91 (d, 1H, J=8.2 Hz), 6.50 (dd, 1H, $J_1$=8.2 Hz, $J_2$=2.4 Hz), 6.31 (m, 2H), 6.13 (br s, 1H), 4.71 (d, 2H, J=2.2 Hz), 4.08 (m, 2H), 3.05 (m, 2H), 2.24 (m, 2H), 1.91 (m, 1H), 1.70 (m, 2H), 1.54 (m, 1H), 1.41 (m, 2H), 1.30 (m, 2H). ESI(+)=463.3 $(M+H)^+$. Calculated mass: 462.18.

((1-Carboxy-5-(3-(4-(prop-2-yn-1-yloxy)phenyl)ureido)pentyl)carbamoyl)glutamic acid (8). Alkyne (5) was deprotected by the same method and the title compound was isolated as a white powder (96%). $^1H$ NMR (500 MHz, DMSO-d6) δ 8.28 (s, 1H), 7.31 (d, 2H, J=9.0 Hz), 6.87 (d, 2H, J=9.0 Hz), 6.35 (d, 1H, J=11.4 Hz), 6.34 (d, 1H, J=11.4 Hz), 6.09 (br s, 1H), 4.72 (d, 2H, J=2.3 Hz), 4.10 (m, 2H), 3.54 (t, 1H, J=2.3 Hz), 3.06 (m, 2H), 2.25 (m, 2H), 1.93 (m, 1H), 1.63 (m, 2H), 1.53 (m, 1H), 1.42 (m, 2H), 1.31 (m, 2H). ESI(+)=493.3 $(M+H)^+$. Calculated mass: 492.19.

Route B Synthesis (((S)-5-Amino-1-carboxypentyl)carbamoyl)-L-glutamic acid (9). Compound (1) (1.22 g, 2.5 mmol) was dissolved in $CH_2Cl_2$ (5 mL). Trifluoroacetic acid (1.5 mL) was added, and the reaction was stirred overnight at room temperature. The volatile materials were removed under a stream of N2, and the crude product was lyophilized to give (((S)-amino-1-carboxypentyl)carbamoyl)-L-glutamic acid (9) as a viscous oil (700 mg, 88%). $^1H$ NMR (500 MHz, DMSO-d6) δ

7.71 (s, 2H), 6.37 (m, 2H), 4.08 (m, 2H), 2.78 (m, 2H), 2.25 (m, 2H), 1.93 (m, 1H), 1.70 (m, 2H), 1.53 (m, 3H), 1.32 (m, 2H).

(((S)-1-Carboxy-5-(3-(2-ethynylphenyl)ureido)pentyl) carbamoyl)-L-glutamic acid (10). A solution of 2-ethynyl aniline (30 µL, 0.26 mmol) in toluene (1 mL) was added slowly to a solution of triphosgene (56 mg, 0.19 mmol) in toluene (3 mL) at room temperature under Ar. Triethylamine (42 µL, 0.30 mmol) was added and the reaction was heated to reflux for 6 h. The solvent was removed under reduced pressure, and the crude residue, a yellow/white semisolid, was dissolved in DMF (2 mL). Then a solution of amine (9) (60 mg, 0.19 mmol) in DMF (1 mL) was added, followed by triethylamine (42 µL, 0.30 mmol). The reaction was stirred at room temperature for 90 min. The mixture was concentrated under reduced pressure and the crude residue was purified by reverse phase prep HPLC (12 mL/min, 0% B to 100% B over 30 min followed by 5 min at 100% B; X=220 nm, 254 nm). The peak containing the product was collected and lyophilized to give (((S)-1-carboxy-5-(3-(2-ethynylphenyl)ureido)pentyl)carbamoyl)-L-glutamic acid (10) as a white powder (27 mg, 31% yield). $^{1}$H NMR (500 MHz, DMSO-d6) δ 8.13 (d, 1H, J=8.5 Hz), 7.86 (s, 1H), 7.37 (dd, 1H, $J_1$=7.6 Hz, $J_2$=1.3 Hz), 7.27 (m, 1H), 7.23 (br s, 1H), 6.90 (t, 1H, J=7.6 Hz), 6.34 (m, 2H), 4.56 (s, 1H), 4.10 (m, 2H), 3.08 (m, 2H), 2.25 (m, 2H), 1.93 (m, 1H), 1.70 (m, 2H), 1.57 (m, 1H), 1.44 (m, 2H), 1.33 (m, 2H). ESI(+)=463.5 $(M+H)^+$; ESI(−)=461.2 $(M-H)^-$. Calculated mass: 462.18.

((1-Carboxy-5-(3-(3-(prop-2-yn-1-yloxy)phenyl)ureido) pentyl)carbamoyl) glutamic acid (11). The compound was synthesized by the same method from amine (9) and 3-(prop-2-yn-1-yloxy)aniline and isolated as a light brown powder (13%). $^{1}$H NMR (500 MHz, DMSO-d6) δ 8.54 (s, 1H), 7.61 (s, 1H), 7.32 (dd, 1H, $J_1$=8.1 Hz, $J_2$=1.3 Hz), 7.21 (t, 1H, J=7.8 Hz), 6.98 (d, 1H, J=7.6 Hz), 6.33 (m, 2H), 6.21 (br s, 1H), 4.11 (s, 2H), 4.08 (m, 2H), 3.06 (m, 2H), 2.24 (m, 2H), 1.93 (m, 1H), 1.71 (m, 2H), 1.55 (m, 1H), 1.43 (m, 2H), 1.31 (m, 2H). ESI(+)=493.1 $(M+H)^+$. Calculated mass: 492.19.

(((S)-1-carboxy-5-(3-(4-ethynylphenyl)ureido)pentyl) carbamoyl)-L-glutamic acid (12). The compound was synthesized by the same method from amine (9) and 4-ethynyl aniline and isolated as a pale green powder (38%). $^{1}$H NMR (500 MHz, DMSO-d6) δ 8.64 (s, 1H), 7.40 (d, 2H, J=8.5 Hz), 7.32 (d, 2H, J=8.5 Hz), 6.33 (m, 2H), 6.22 (br s, 1H), 4.10 (m, 2H), 3.99 (s, 1H), 3.07 (m, 2H), 2.25 (m, 2H), 1.93 (m, 1H), 1.70 (m, 2H), 1.55 (m, 1H), 1.43 (m, 2H), 1.31 (m, 2H). ESI(+)=463.4 $(M+H)^+$; ESI(−)=461.3 $(M-H)^-$. Calculated mass: 462.18.

Representative $^{19}$F Compounds from the Representative Intermediates

Representative synthetic procedures are provided below in Scheme 3 in generating exemplary $^{19}$F compounds illustrative of $^{18}$F compounds of the present technology, followed by a more detailed description of the synthesis of these exemplary $^{19}$F compounds.

Scheme 3.

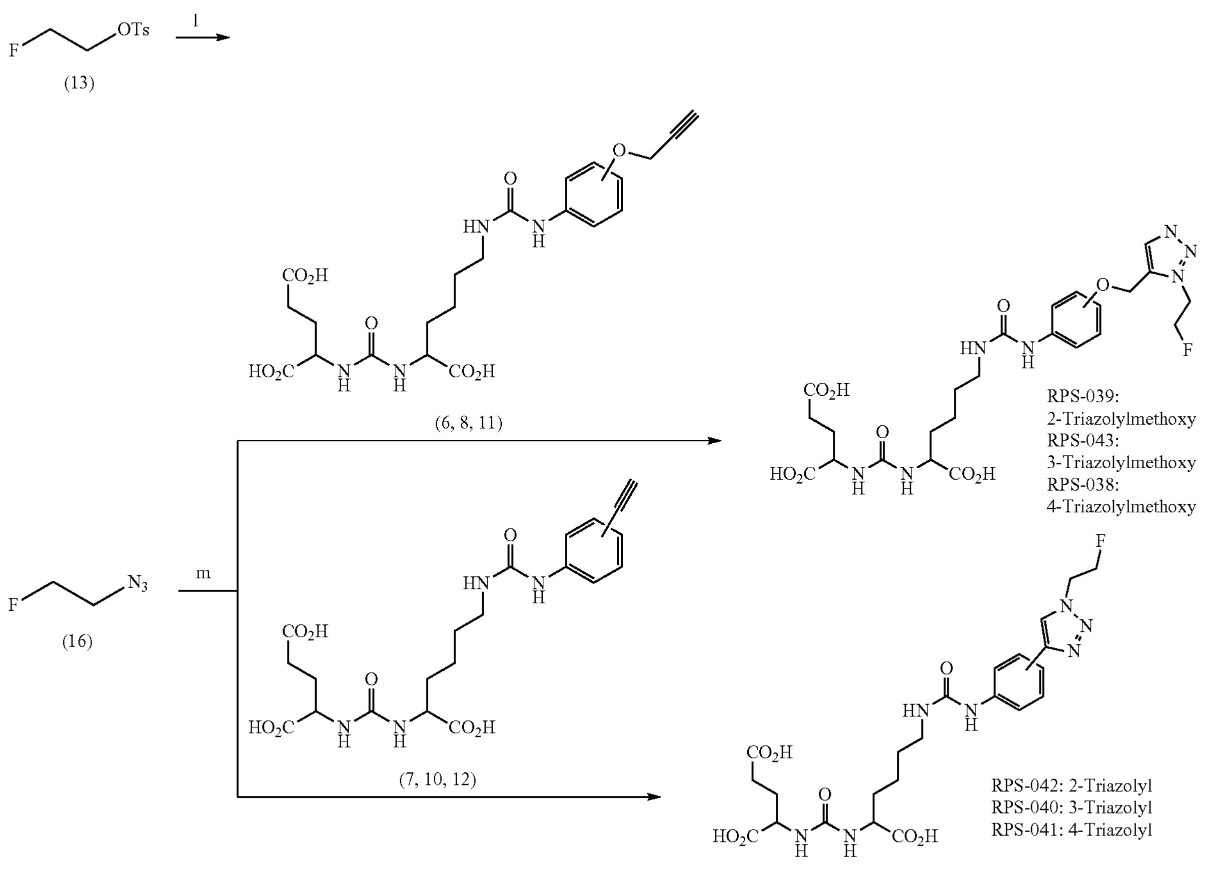

(13)
(16)
(6, 8, 11)
(7, 10, 12)
RPS-039: 2-Triazolylmethoxy
RPS-043: 3-Triazolylmethoxy
RPS-038: 4-Triazolylmethoxy
RPS-042: 2-Triazolyl
RPS-040: 3-Triazolyl
RPS-041: 4-Triazolyl 2-Fluoroethyltosylate (13). A solution of tetrabutylammonium fluoride (2.2 mL, 1.0M in TIF) was added to a suspension of di(p-toluenesulfonyl)ethanediol (740 mg, 2.0 mmol) in THE (15 mL), and the mixture was heated to reflux under Ar overnight. Then the reaction was cooled to room temperature and the solvent was removed under reduced pressure. The crude residue was partitioned between $H_2O$ and EtOAc. The layers were separated and the aqueous layer was extracted with EtOAc. The organic layers were combined and dried over $MgSO_4$, filtered and concentrated under reduced pressure to give a colorless oil. The oil was purified by silica chromatography (20% EtOAc in hexanes) to give 2-fluoroethyltosylate (13) as a colorless oil (225 mg, 52% yield). $^1H$ NMR (500 MHz, $CDCl_3$) δ 7.79 (d, 2H, J=8.5 Hz), 7.35 (d, 2H, J=8.6 Hz), 4.61 (m, 1H), 4.51 (m, 1H), 4.28 (m, 1H), 4.22 (m, 1H), 2.45 (s, 3H).

(((S)-1-Carboxy-5-(3-(2-(1-(2-fluoroethyl)-1H-1,2,3-triazol-4-yl)phenyl)ureido)pentyl)carbamoyl)-L-glutamic acid (RPS-042). Sodium azide (10 mg, 150 μmol) was suspended in a solution of 2-fluoroethyltosylate (7.5 mg, 30 μmol) in DMF (0.3 mL). The suspension was stirred overnight at room temperature and then filtered. To the filtrate was added a solution of alkyne (6) (0.9 mg, 1.83 μmol) in DMSO (0.2 mL). In a separate vial, 0.5M $CuSO_4$ (100 μL) and 1.5M sodium ascorbate (100 μL) were mixed for 5 min and then transferred to the reaction vial as a solution in DMF (100 μL). The reaction was stirred for 60 min at room temperature and was then purified by reverse phase prep HPLC (12 mL/min, 0% B to 100% B over 30 min followed by 5 min at 100% B; X=220 nm, 254 nm). The peak containing the product was lyophilized, and RPS-042 was isolated as a white powder (0.8 mg, 75% yield). $^1H$ NMR (500 MHz, DMSO-d6) δ 8.64 (s, 1H), 8.16 (d, 1H, J=8.1 Hz), 7.61 (d, 1H, J=7.8 Hz), 7.26 (dd, 1H, $J_1$=8.3 Hz, $J_2$=7.3 Hz), 7.12 (br s, 1H), 7.02 (m, 2H), 6.33 (d, 1H, J=8.3 Hz), 6.31 (d, 1H, J=8.4 Hz), 4.97 (m, 1H), 4.86 (m, 2H), 4.80 (m, 1H), 4.10 (m, 2H), 3.07 (m, 2H), 2.25 (m, 2H), 1.94 (m, 1H), 1.70 (m, 2H), 1.57 (m, 1H), 1.44 (m, 2H), 1.32 (m, 2H). ESI(+)=552.4 $(M+H)^+$; ESI(−)=550.3 $(M-H)^-$. Calculated mass: 551.21.

(((S)-1-Carboxy-5-(3-(3-(1-(2-fluoroethyl)-1H-1,2,3-triazol-4-yl)phenyl)ureido)pentyl)carbamoyl)-L-glutamic acid (RPS-040). RPS-040 was synthesized from alkyne (7) by the same method as RPS-042 and isolated as a white powder (82% yield). $^1H$ NMR (500 MHz, DMSO-d6) δ 8.52 (s, 2H), 7.94 (s, 1H), 7.32 (m, 2H), 7.26 (m, 1H), 6.32 (m, 2H), 6.15 (t, 1H, J=5.2 Hz), 4.91 (t, 1H, J=4.6 Hz), 4.82 (t, 1H, J=4.6 Hz), 4.77 (t, 1H, J=4.6 Hz), 4.71 (t, 1H, J=4.6 Hz), 4.08 (m, 2H), 3.07 (d, 2H, $J_1$=12.4 Hz, $J_2$=6.8 Hz), 2.25 (m, 2H), 1.91 (m, 1H), 1.67 (m, 2H), 1.54 (m, 1H), 1.43 (m, 2H), 1.30 (m, 2H). ESI(+)=552.4 $(M+H)^+$. ESI(−)=550.3. Calculated mass: 551.21.

(((S)-1-Carboxy-5-(3-(4-(1-(2-fluoroethyl)-1H-1,2,3-triazol-4-yl)phenyl)ureido)pentyl)carbamoyl)-L-glutamic acid (RPS-041). RPS-041 was synthesized from alkyne (8) by the same method as RPS-042 and isolated as a white powder (50% yield). $^1H$ NMR (500 MHz, DMSO-d6) δ 8.57 (s, 1H), 8.48 (s, 1H), 7.70 (d, 2H, J=8.6 Hz), 7.47 (d, 2H, J=8.6 Hz), 6.35 (d, 1H, J=9.3 Hz), 6.33 (d, 1H, J=9.3 Hz), 6.22 (br s, 1H), 4.92 (t, 1H, J=4.7 Hz), 4.83 (t, 1H, J=4.7 Hz), 4.77 (t, 1H, J=4.7 Hz), 4.72 (t, 1H, J=Hz), 4.10 (m, 2H), 3.10 (m, 2H), 2.21 (m, 2H), 1.93 (m, 1H), 1.85 (m, 2H), 1.63 (m, 1H), 1.43 (m, 2H), 1.33 (m, 2H). ESI(+)=552.5 $(M+H)^+$; ESI(−)=550.3 $(M-H)^-$. Calculated mass: 551.21.

(((S)-1-Carboxy-5-(3-(2-((1-(2-fluoroethyl)-1H-1,2,3-triazol-4-yl)methoxy)phenyl)ureido)pentyl)carbamoyl)-L-glutamic acid (RPS-039). RPS-039 was synthesized from alkyne (10) by the same method as RPS-042 and isolated as a white powder (34% yield). $^1H$ NMR (500 MHz, DMSO-d6) δ 8.30 (s, 1H), 8.09 (d, 1H, J=9.7 Hz), 7.74 (s, 1H), 7.16 (d, 1H, J=9.6 Hz), 6.95 (t, 1H, J=5.4 Hz), 6.86 (m, 2H), 6.32 (m, 2H), 5.24 (s, 2H), 4.90 (t, 1H, J=4.4 Hz), 4.78 (m, 2H), 4.72 (t, 1H, J=4.4 Hz), 4.10 (m, 2H), 3.05 (m, 2H), 2.25 (m, 2H), 1.93 (m, 1H), 1.71 (m, 2H), 1.55 (m, 1H), 1.40 (m, 2H), 1.32 (m, 2H). ESI(+)=582.4 $(M+H)^+$; ESI(−)=580.3 $(M-H)^-$. Calculated mass: 581.22.

(((S)-1-Carboxy-5-(3-(3-((1-(2-fluoroethyl)-1H-1,2,3-triazol-4-yl)methoxy)phenyl)ureido)pentyl)carbamoyl)-L-glutamic acid (RPS-043). RPS-043 was synthesized from alkyne (11) by the same method as RPS-042 and isolated as a white powder (60% yield). $^1H$ NMR (500 MHz, DMSO-d6) δ 8.40 (s, 1H), 8.25 (s, 1H), 7.18 (br s, 1H), 7.10 (t, 1H, J=8.1 Hz), 6.89 (d, 1H, J=8.1 Hz), 6.57 (d, 1H, J=8.2 Hz), 6.31 (m, 2H), 6.13 (br s, 1H), 5.09 (s, 1H), 4.87 (t, 1H, J=4.6 Hz), 4.76 (m, 2H), 4.69 (t, 1H, J=4.6 Hz), 4.08 (m, 2H), 3.05 (m, 2H), 2.24 (m, 2H), 1.91 (m, 1H), 1.69 (m, 2H), 1.55 (m, 1H), 1.40 (m, 2H), 1.31 (m, 2H). ESI(+)=582.4 $(M+H)^+$; ESI(−)=580.2 $(M-H)^-$. Calculated mass: 581.22.

(((S)-1-Carboxy-5-(3-(4-((1-(2-fluoroethyl)-1H-1,2,3-triazol-4-yl)methoxy)phenyl)ureido)pentyl)carbamoyl)-L-glutamic acid (RPS-038). RPS-038 was synthesized from alkyne (12) by the same method as RPS-042 and isolated as a white powder (77% yield). $^1H$ NMR (500 MHz, DMSO-d6) δ 8.27 (s, 1H), 8.25 (s, 1H), 7.30 (d, 2H, J=9.0 Hz), 6.91 (d, 2H, J=9.0 Hz), 6.34 (m, 2H), 6.10 (t, 1H, J=5.3 Hz), 5.09 (s, 2H), 4.89 (t, 1H, J=4.5 Hz), 4.78 (m, 2H), 4.71 (t, 1H, J=4.5 Hz), 4.10 (m, 2H), 3.06 (m, 2H), 2.25 (m, 2H), 1.93 (m, 1H), 1.73 (m, 2H), 1.60 (m, 1H), 1.42 (m, 2H), 1.32 (m, 2H). ESI(+)=582.3 $(M+H)^+$; ESI(−)=580.3 $(M-H)^-$. Calculated mass: 581.22.

Synthesis of DCFPyL

The synthesis of the cold ligand DCFPyL and the precursor trimethylammonium salt prosthetic group (20) were undertaken according to procedures described in Olberg D E, Arukwe J M, Grace D, Hjelstuen O K, Solbakken M, Kindberg G M, Cuthbertson A. One Step Radiosynthesis of 6-[$^{18}$F]Fluoronicotinic Acid 2,3,5,6-Tetrafluorophenyl Ester ([$^{18}$F]F-Py-TFP): A New Prosthetic Group for Efficient Labeling of Biomolecules with Fluorine-18. J Med Chem. 2010; 53:1732-40 and Chen Y, Pallumbhatla M, Foss C A, Byun Y, Nimmagadda S, Senthamizhchelvan S, et al. 2-(3-{1-Carboxy-5-[(6-[$^{18}$F]Fluoro-Pyridine-3-Carbonyl)-Amino]-Pentyl}-Ureido)-Pentanedioic Acid, [$^{18}$F]DCFPyL, a PSMA-Based PET Imaging Agent for Prostate Cancer. Clin Cancer Res. 2011; 17:7645-53, each of which is incorporated herein by reference.

N,N,N-Trimethyl-5-((2,3,5,6-tetrafluorophenoxy)-carbonyl)pyridine-2-aminium trifluoromethanesulfonate (20). The title compound was isolated in three steps from 6-chloronicotinic acid as white crystals (137 mg, 19% yield). $^1H$ NMR (500 MHz, $CDCl_3$) δ 9.42 (d, 1H, J=2.2 Hz), 8.94 (dd, 1H, $J_1$=8.7 Hz, $J_2$=2.2 Hz), 8.29 (d, 1H, J=8.7 Hz), 7.57 (m, 1H), 3.76 (s, 9H). ESI(+)=329.3 ($M^+$-OTf). Calculated mass: 329.09.

6-Fluoronicotinic acid 2,3,5,6-tetrafluorophenyl ester (21). The title compound was synthesized from trimethylammonium salt (20) as a white powder (2.5 mg, 14% yield). $^1H$ NMR (500 MHz, $CDCl_3$) δ 9.11 (d, 1H, J=2.1 Hz), 8.59 (dt, 1H, $J_1$=8.2 Hz, $J_2$=2.4 Hz), 7.15 (dd, 1H, $J_1$=8.6 Hz, $J_2$=2.9 Hz), 7.10 (m, 1H).

2-(3-{1-Carboxy-5-[(6-fluoropyridine-3-carbonyl)-amino]-pentyl}-ureido)-pentanedioic acid (DCFPyL). The title compound was synthesized from the activated ester (21) in two steps as a white powder (2.0 mg, 55% yield). $^1H$ NMR (500 MHz, DMSO-d6) δ 8.67 (m, 2H), 8.38 (m, 1H), 7.30 (dd, 1H, $J_1$=8.6 Hz, $J_2$=2.6 Hz), 6.33 (m, 2H), 4.08 (m, 2H), 3.26 (m, 2H), 2.25 (m, 2H), 1.93 (m, 1H), 1.72 (m, 2H), 1.58 (m, 3H), 1.36 (m, 2H). ESI(+)=499.4 $(M+H)^+$. Calculated mass: 498.21

Radiosynthesis

General Methods. All solvents and reagents were purchased from Sigma Aldrich and were of reagent grade quality unless otherwise indicated. All reactions were carried out in oven dried glassware. Fluorine-18 was obtained by irradiation of $H_2{}^{18}O$ (Rotem Industries) via the $^{18}O(p,n)$ $^{18}F$ transformation using a TR19 cyclotron (Advanced Cyclotron Systems, Inc.). End-of-bombardment activity was typically 5.55-9.25 GBq (150-250 mCi). Analytical and semi-preparative HPLC were performed on a dual pump Varian HPLC (Agilent Technologies) fitted with a dual UV-Vis detector and a NaI(Tl) detector (Bioscan). Solvent A was 0.01% TFA in $H_2O$ and solvent B was 0.01% TFA in 90:10 v/v MeCN:$H_2O$. Semi-prep HPLC was performed on a Bondapak C18 7.8×300 mm 125 Å column (Waters) while analytical HPLC was performed on a Symmetry C18 4.6×50 mm 100 Å column (Waters). The UV absorption spectrum was monitored at 220 nm and 280 nm. Semi-prep HPLC was performed using an isocratic solvent mixture of 15% B at a flow rate of 4 mL/min. Analytical HPLC was generally performed at a flow rate of 2 ml/min using the following gradient; 0% B 0-1 min., 0-100% B 1-8 mins., 100-0% B 8-10 mins. All radiochemical yields were corrected to the [$^{18}$F]fluoride activity measured at start-of-synthesis. The reaction conditions reported represent the highest yields obtained using manual radiosyntheses.

Radiosynthesis of Exemplary $^{18}$F Compounds of the Present Technology

A representative synthetic scheme for certain exemplary $^{18}$F compounds of the present technology is presented below in Scheme 4. Particular procedural details follow thereafter.

Scheme 4.

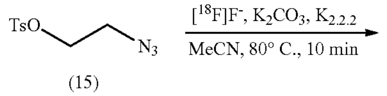

(15)

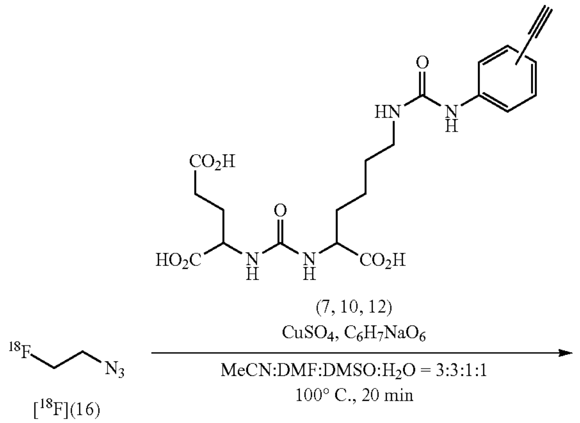

[$^{18}$F](16)

-continued

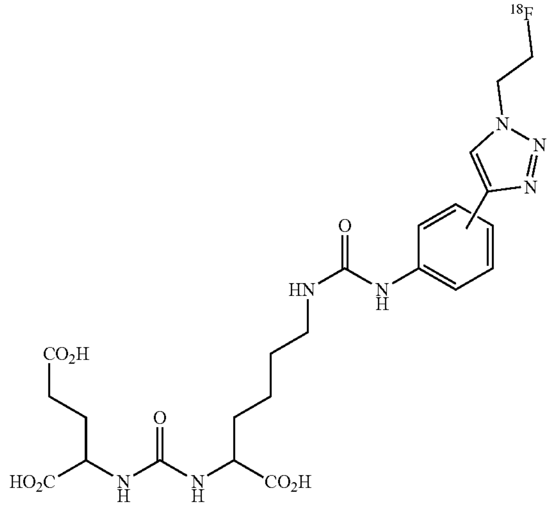

[$^{18}$F]RPS-042 = 2-Triazolyl
[$^{18}$F]RPS-040 = 3-Triazolyl
[$^{18}$F]RPS-041 = 4-Triazolyl

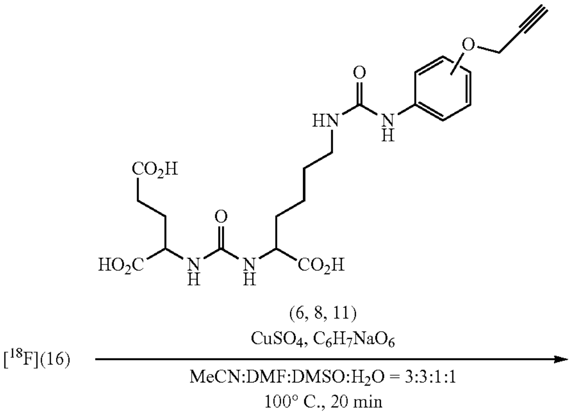

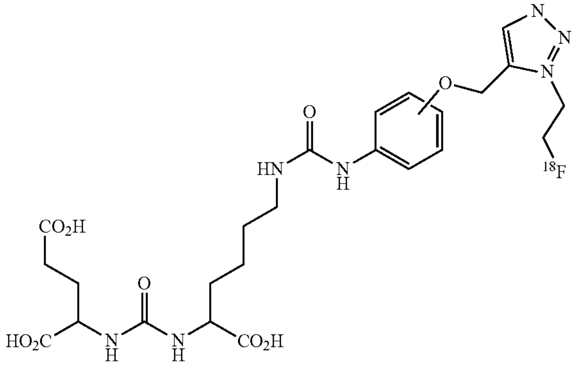

[$^{18}$F]RPS-039 = 2-Triazolylmethoxy
[$^{18}$F]RPS-043 = 3-Triazolylmethoxy
[$^{18}$F]RPS-038 = 4-Triazolylmethoxy 2-Azidoethanol (14). Bromoethanol (250 mg, 2.0 mmol) was dissolved in $H_2O$ (7 mL). A solution of sodium azide (195 mg, 3.0 mmol) in $H_2O$ (3 mL) was added, and the reaction was stirred for 4 h at room temperature and then 16 h at 80° C. Then the reaction was cooled to room temperature and extracted with EtOAc. The organic layers were combined, dried over $MgSO_4$, filtered and concentrated under reduced pressure to give 2-azidoethanol (14) as a clear liquid (149 mg, 86% yield). $^1H$ NMR (500 MHz, $CDCl_3$) δ 3.88 (t, 2H, J=5.1 Hz), 3.39 (t, 2H, J=5.1 Hz), 3.14 (br s, 1H).

2-Azidoethyltosylate (15). A solution of p-toluenesulfonyl chloride (394 mg, 2.07 mmol) in $CH_2Cl_2$ (5 mL) was added to a solution of 2-azidoethanol (149 mg, 1.72 mmol) in $CH_2Cl_2$ (10 mL). Triethylamine (0.48 mL, 3.44 mmol) was added, and the reaction was stirred for 5 h at room temperature under Ar. Then the reaction was washed successively with 1M HCl, $H_2O$ and saturated NaCl solution. The organic layer was dried over $MgSO_4$, filtered and concentrated under reduced pressure to give a pale oil. The oil was purified by silica chromatography (33% EtOAc in hexanes) to give 2-azidoethyltosylate (15) as a colorless oil (204 mg, 49% yield). $^1H$ NMR (500 MHz, $CDCl_3$) δ 7.74 (d, 2H, J=8.2 Hz), 7.29 (d, 2H, J=8.1 Hz), 4.08 (t, 2H, J=5.1 Hz), 3.41 (t, 2H, J=5.1 Hz), 2.39 (s, 3H).

2-[$^8$F]fluoroethylazide (16). No-carrier-added [$^{18}$F]fluoride was trapped on a pre-activated Sep-Pak QMA cartridge (Waters) and eluted with 1 mL of an 80% v/v MeCN/$H_2O$ solution containing 2.7 mg $K_2CO_3$ and 4 mg Kryptofix-222. The solution was dried azeotropically with MeCN (2×0.5 mL) at 100° C. in 10 min. To the dried [$^{18}$F]fluoride was added a solution of 2-azidoethyltosylate (15) (6 mg) in MeCN (300 μL). The resulting solution was stirred at 80° C. for 10 min to yield 2-[$^{18}$F]fluoroethylazide. The 2-[$^{18}$F]fluoroethylazide was purified by distillation by heating the vial at 130° C. and trapping the 2-[$^{18}$F]fluoroethylazide in a vial containing 100 μL DMF cooled to 0° C.

Exemplary Synthesis of Representative $^{18}$F Compounds of the Present Technology.

A pre-mixed solution of 0.5M $CuSO_4$ (50 μL) and 1.5M sodium ascorbate (50 μL) in DMF (100 μL) was added to the vial containing the 2-[$^{18}$F]fluoroethylazide solution followed by 1 mg alkyne precursor (6-8; 10-12) in DMSO (100-150 μL). The reaction was stirred at 100° C. for 20 min. It was then cooled to room temperature, diluted with 2 mL $H_2O$ and filtered through a 0.45 μm nylon syringe filter (Cole-Parmer). The filter was washed with 1 mL $H_2O$, which was added to the filtrate. The filtrate was purified by semi-prep reverse phase HPLC (4 mL/min; 0-100% B; 30 min), and the peak corresponding to $^{18}$F-labeled triazole was collected, diluted with $H_2O$ and passed through a pre-activated Oasis™ solid phase extraction cartridge (Waters). The retained activity was eluted with EtOH and diluted with 0.9% NaCl solution until the concentration of ethanol was less than 5% v/v and the radioactivity concentration was a minimum of 74 MBq/mL. The synthesis, purification and final formulation were achieved in 105 min from start-of-synthesis. An optimized isocratic HPLC purification method (4 mL/min; 15% B; 30 min) was used to isolate [$^{18}$F]RPS-040 and [$^{18}$F]RPS-041 in 20-40% decay corrected radiochemical yield, greater than 99% radiochemical purity and a specific activity of up to 391 GBq/μmol.

[$^{68}$Ga]Ga-PSMA-HBED-CC. The title compound was generated according to the procedure described in Amor-Coarasa A, Schoendorf M, Meckel M, Vallabhajosula S, Babich J. Comprehensive Quality Control of the ITG Ge-68/Ga-68 Generator and Synthesis of Ga-68-DOTATOC and Ga-68-PSMA-HBED-CC for Clinical Imaging. J Nucl Med. 2016 Apr. 21 (PMID: 27103024), incorporated herein by reference. In particular, a 1.85 GBq $^{68}$Ga/$^{68}$Ge Generator (ITG) was eluted with 4 mL 0.05M HCl, and $^{68}GaCl_3$ was obtained as a 185-222 MBq/mL solution. From this stock solution was taken 1 mL (containing approximately 185 MBq), which was combined with 5 μL of a 1 mg/mL solution of PSMA-HBED-CC (ABX) in $H_2O$ at 95° C. The reaction was initiated by the addition of 20 μL of a 3N NaOAc solution, and heating to 95° C. continued for 20 min on a Thermomixer. It was then passed through a pre-activated Sep-Pak Oasis™ cartridge (Waters), and the cartridge was washed with $H_2O$. [68Ga]Ga-PSMA-HBED-CC was eluted in a solution of 10% v/v EtOH in saline and diluted to a final concentration of approximately 100 MBq/mL. Decay-corrected radiochemical yield was greater than 95% and radiochemical purity was greater than 99%.

[$^{18}$F]DCFPyL. 10.73 GBq (290 mCi) [$^{18}$F]Fluoride in 2 mL $H_2{}^{18}O$ was dried azeotropically with MeCN at 100° C. in the presence of 50 μL of a 100 μg/mL solution of KF in $H_2O$ and 4 mg kryptofix-222. To the dried mixture was added 9 mg 6-trimethylammonium salt (20) in 1 mL MeCN, and the reaction was stirred at 40° C. for 70 min. The reaction mixture was diluted with 10 mL and passed through a pre-activated Sep-Pak Silica cartridge (Waters). The eluate was evaporated to dryness at 60° C. To the dried mixture was added 1 mg di-tert-butyl (((S)-6-amino-1-(tert-butyoxy)-1-oxohexan-2-yl)carbamoyl)-L-glutamate (1) in 10 μL MeCN, 5 μL $NEt_3$ and 1 mL $CH_2Cl_2$. The reaction was stirred for 20 min at 40° C. and then another 1 mg (1) in 10 μL MeCN and 5 μL $NEt_3$ were added. The reaction was stirred for a further 30 min before the solvent was evaporated and the crude product was dissolved in 100 μL TFA and stirred for 20 min at 40° C. The volatiles were evaporated under vacuum and the crude residue was dissolved in $H_2O$ and purified by semi-prep HPLC (2 mL/min, 10 min gradient). The peak containing the product was collected, diluted with $H_2O$ and trapped on a pre-activated Sep-Pak Oasis™ cartridge (Waters). The activity was eluted with 600 μL MeCN and concentrated at 100° C. under vacuum. The crude residue was dissolved in 200 μL 0.9% NaCl solution. Total synthesis time was 230 minutes, and decay corrected radiochemical yield was 0.9%, radiochemical purity was greater than 96% and the specific activity was greater than 35 GBq/μmol.

Representative Biological Assays

Cell Culture. The human prostate cancer cell line, LNCaP, was obtained from the American Type Culture Collection. Cell culture supplies were from Invitrogen unless otherwise noted. LNCaP cells were maintained in RPMI-1640 medium supplemented with 10% fetal bovine serum (Hyclone), 4 mM L-glutamine, 1 mM sodium pyruvate, 10 mM N-2-hydroxyethylpiperazine-N-2-ethanesulfonic acid (HEPES), 2.5 mg/mL D-glucose, and 50 μg/mL gentamicin in a humidified incubator at 37° C./5% C02. Cells were removed from flasks for passage or for transfer to 12-well assay plates by incubating them with 0.25% trypsin/ethylenediaminetetraacetic acid (EDTA).

In vitro determination of $IC_{50}$. $IC_{50}$ values of the non-radioactive fluorine-containing ligands were determined by screening in a multi-concentration competitive binding assay against $^{99m}$Tc-((7S,12S,16S)-1-(1-(carboxymethyl)-1H-imidazol-2-yl)-2-((1-(carboxymethyl)-1H-imidazol-2-yl)methyl)-9,14-dioxo-2,8,13,15-tetraazaoctadecane-7,12,16,18-tetracarboxylic acid technetium tricarbonyl complex) ($^{99m}$Tc-MIP-1427) for binding to PSMA on LNCaP cells, according to methods previously described. See Hillier S M, Maresca K P, Lu G, Merkin R D, Marquis J C, Zimmerman C N, Eckelman W C, Joyal J L, Babich J W. 99mTc-Labeled Small-Molecule Inhibitors of Prostate-Specific Membrane Antigen for Molecular Imaging of Prostate Cancer. J. Nucl. Med. 2013, 54, 1369-1376, incorporated herein by reference. The LNCaP cells were plated 48 hours prior to the experiment to achieve a density of approximately $5\times10^5$ cells/well (in triplicate) in RPMI-1640 medium supplemented with 0.25% bovine serum albumin prior to performing the assay. LNCaP cells were incubated for 1 hour with 1 nM $^{99m}$Tc-MIP-1427 in serum free RPMI-1640 medium in the presence of 1-10,000 nM test compounds. Radioactive incubation media was then removed by pipette and the cells were washed twice using 1 mL ice-cold HEPES buffer. Cells were harvested from the plates and transferred to tubes for radioactive counting using a Packard Cobra II Gamma Counter. $IC_{50}$ values were determined by non-linear regression using GraphPad Prism software.

Inoculation of mice with xenografts. All animal studies were approved by the Institutional Animal Care and Use Committee of Weill Cornell Medicine and were undertaken in accordance with the guidelines set forth by the USPHS Policy on Humane Care and Use of Laboratory Animals. Animals were housed under standard conditions in approved facilities with 12 h light/dark cycles. Food and water was provided ad libitum throughout the course of the studies. Male inbred athymic nu/nu mice were purchased from The Jackson Laboratory. For inoculation in mice, LNCaP cells were suspended at 4×10$^7$ cells/mL in a 1:1 mixture of PBS:Matrigel (BD Biosciences). Each mouse was injected in the left flank with 0.25 mL of the cell suspension. The mice were imaged when the tumors reached approximately 200-400 mm$^3$, while biodistributions were conducted when tumors were in the range 100-400 mm$^3$.

Imaging. LNCaP xenograft tumor-bearing mice (two per compound) were injected intravenously via the tail vein as a bolus injection of 7.03-7.77 MBq (190-210 μCi) of the tracer ([$^{18}$F]RPS series), 5.5-6.5 MBq (150-175 μCi) [$^{18}$F]DCFPyL or 5.5 MBq (150 μCi) [$^{68}$Ga]Ga-PSMA-HBED-CC. Specific activity was greater than 190 GBq/pmol. The mice were imaged by μPET/CT (Inveon™; Siemens Medical Solutions, Inc.) at 1 h, 2 h, 4 h, and 6 h post-injection ([$^{18}$F]fluorinated compounds) or 1 h and 3 h post-injection ([$^{68}$Ga]Ga-PSMA-HBED-CC). Total acquisition time was thirty minutes, and a CT scan was obtained either immediately before or immediately after the acquisition for both anatomical co-registration and attenuation correction. The data were reconstructed using the commercial Inveon™ software supplied by the vendor. Tumor uptake was estimated by drawing a region of interest (ROI).

Biodistribution. LNCaP xenograft tumor-bearing mice (n=5 per time point) were injected via the tail vein with a bolus injection of 370 kBq (10 μCi) of either [$^{18}$F]RPS-040 or [$^{18}$F]RPS-041. The specific activity of the compounds was 341 GBq/pmol and 391 GBq/pmol, respectively. The mice were euthanized by asphyxiation under isofluorane at 1 h, 2 h and 4 h post injection. An additional set of mice (n=5) was co-administered [$^{18}$F]RPS-040 (370 kBq; 10 μCi) and 2-PMPA (approx. 250 μg; 10 mg/kg) and sacrificed at 1 h post injection to determine the uptake specificity. A full biodistribution study was conducted on all mice, and tissues were excised, weighed and counted in an automated γ-counter. Tissue time-activity values were expressed as percentage injected dose per gram of tissue (% ID/g). Statistical comparisons were performed using the standard Student's t-test for a 95% confidence interval.

Representative Activity of Compounds of the Present Technology

Exemplary in vitro study results. The affinity for PSMA was determined in a competitive binding assay using LNCaP cells, and the $IC_{50}$s of the six compounds ranged from 3.2-36.5 nM (Table 1). In the same LNCaP-based assay, MIP-1095 was determined to have an $IC_{50}$ of 0.3 nM while DCFPyL, a fluorinated PSMA inhibitor currently undergoing first-in-man trials in the United States and Europe had an $IC_{50}$ of 22.8 nM. [$^{68}$Ga]Ga-PSMA-HBED-CC has been reported to have an $IC_{50}$ of approximately 24 nM for PSMA in a competitive binding assay using LNCaP cells.

TABLE 1

| Compound | $IC_{50}$ (nM) | Max. LNCaP Tumor Uptake (% ID/g) | Time p.i. (h) |
|---|---|---|---|
| MIP-1095 | 0.3 | 34.3 ± 12.7[a] | 4 |
| $^{68}$Ga-PSMA-HBED-CC | 24.3 ± 2.0[b] | 6.27 ± 1.44 | 3 |
| DCFPyL | 22.8 | 5.71 ± 0.61[c] | 1 |
| SERIES ONE | | | |
| RPS-039 | 14.0 | 5.89 ± 0.27[c] | 2 |
| RPS-043 | 36.5 | 9.04 ± 1.88[c] | 2 |
| RPS-038 | 21.3 | 8.87 ± 0.64[c] | 2 |
| SERIES TWO | | | |
| RPS-042 | 10.2 | 10.06 ± 1.33[c] | 2 |
| RPS-040 | 7.0 | 14.30 ± 2.49 | 2 |
| RPS-041 | 3.2 | 10.86 ± 1.03 | 2 |

[a]See Maresca K P, Hillier S M, Femia F J, Barone D K C, Joyal J L, Zimmerman C N, Kozikowski A P, Barrett J A, Eckelman W C, Babich J W. A Series of Halogenated Heterodimeric Inhibitors of Prostate Specific Membrane Antigen (PSMA) as Radiolabeled Probes for Targeting Prostate Cancer. J. Med. Chem. 2009, 52, 347-357.
[b]See Wüstemann T, Bauder-Wüst U, Schäfer M, Eder M, Benesova M, Leotta K, Kratochwil C, Haberkorn U, Kopka K, Mier W. Design of Internalizing PSMA-specific Glu-ureido-based Radiotherapeuticals. Theranostics. 2016 Apr. 28; 6(8): 1085-95.
[c]Image derived calculation of tumor uptake In vivo Evaluation. The six representative $^{18}$F compounds of the present technology were assessed in a mouse model of prostate cancer by μPET/CT imaging at 1 h, 2 h, 4 h and 6 h post-injection. Each of the representative $^{18}$F compounds of the present technology showed good tumor uptake by 1 h, with uptake peaking at 2 h and maintaining a steady value up to 4 h (FIG. 1). No significant washout was observed by 6 h. In contrast, signal in other tissues such as the kidneys and liver began to decrease after 1 h, leading to high contrast images by 2 h post injection. Excretion was predominantly via the urine as evidenced by the rapid accumulation of activity in the bladder of these mice. Urine was not collected.

The maximum tumor uptake (t=2 h) for the compounds in Series One was estimated from the μPET/CT images to range from 5.89±0.27% ID/g to 9.04±1.88% ID/g and with uptake of [$^{18}$F]RPS-043>[$^{18}$F]RPS-038>[$^{18}$F]RPS-039 (see Table 1 supra). Uptake did not directly correlate with the $IC_{50}$ determined in LNCaP cells, as RPS-039 had the highest affinity for PSMA (14 nM) in Series One, but the lowest tumor uptake (5.87±0.27% ID/g). Compounds in Series Two showed greater tumor uptake and higher contrast than their Series One structural counterparts. Maximum tumor uptake (t=2 h) was derived from the image and calculated to range from 10.06±1.33% ID/g to 14.30±0.67% ID/g and in the order [$^{18}$F]RPS-040>[$^{18}$F]RPS-041>[$^{18}$F]RPS-042 (see Table 1 supra). It was again the case that the highest affinity compound ([$^{18}$F]RPS-041; $IC_{50}$=3.2 nM) did not have the highest tumor uptake.

The major route of clearance appeared to be via the kidneys, with the exception of RPS-039 and RPS-042, which showed clearance via the hepatobiliary pathway in addition to renal clearance. These two compounds share substitution at the 2-position of the phenylurea as a structural feature. While [$^{18}$F]RPS-039 was the most potent Series One compound in the in vitro binding assay, both [$^{18}$F]RPS-039 and [$^{18}$F]RPS-042 had the lowest tumor uptake and lowest image contrast of their respective series.

[$^{18}$F]RPS-040 and [$^{18}$F]RPS-041, which had both the highest image-derived tumor uptake (14.30% ID/g and 12.51% ID/g, respectively) and greatest tumor/background contrast in the pPET/CT images, were evaluated further by biodistribution studies in LNCaP tumor xenograft-bearing mice.

Figure 2:
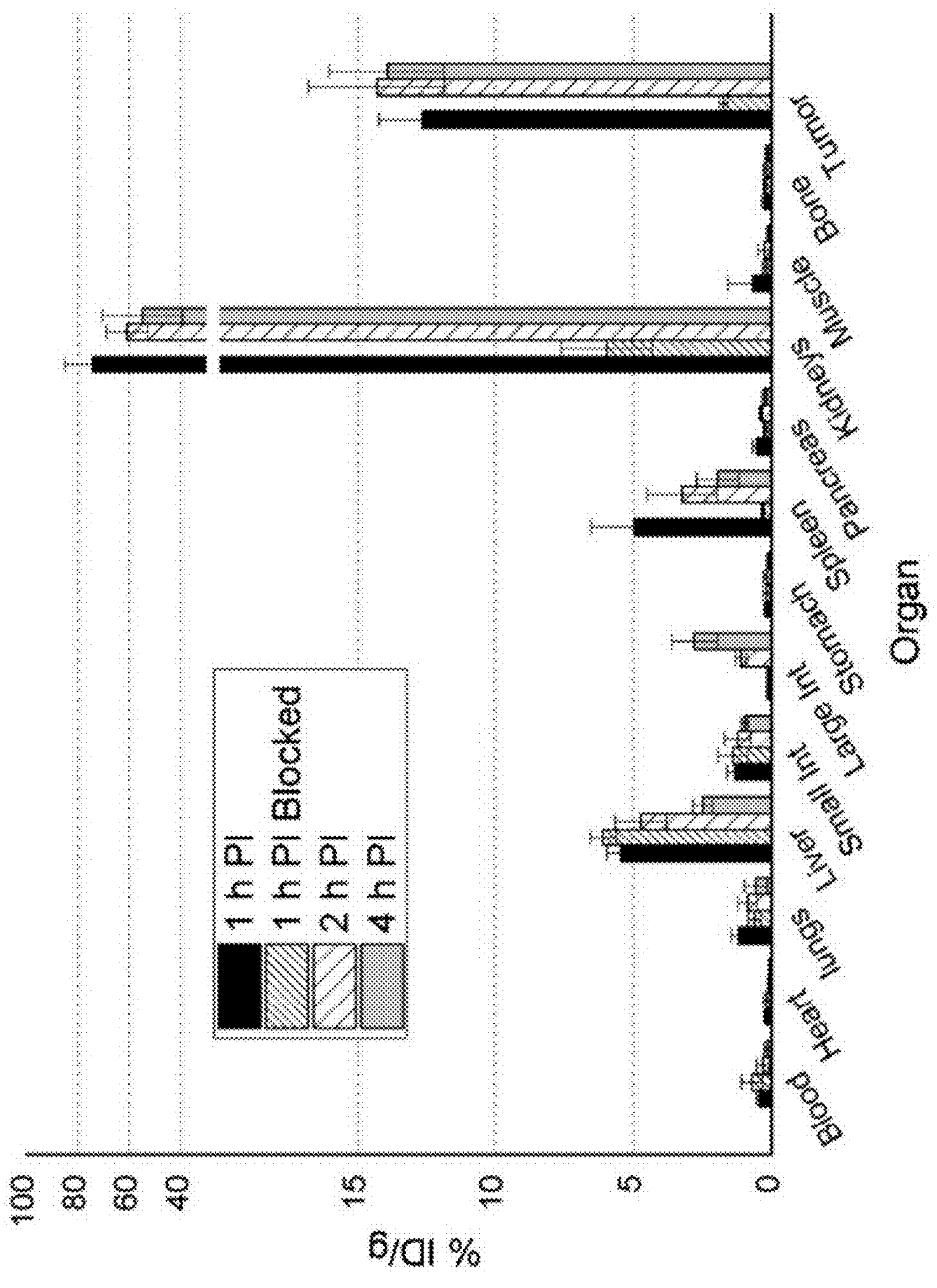
FIG. 2 provides the biodistribution of [$^{18}$F]RPS-040 (of the present technology) in LNCaP xenograft-tumor bearing mice. Mice (n=5 per time point) were sacrificed at 1 h (1 h PI), 2 h (2 h PI) and 4 h (4 h PI) post injection. To determine specificity for PSMA, 2-PMPA was co-administered and the mice were sacrificed at 1 h post injection (n=5; 1 h PI Blocked).
Figure 3:
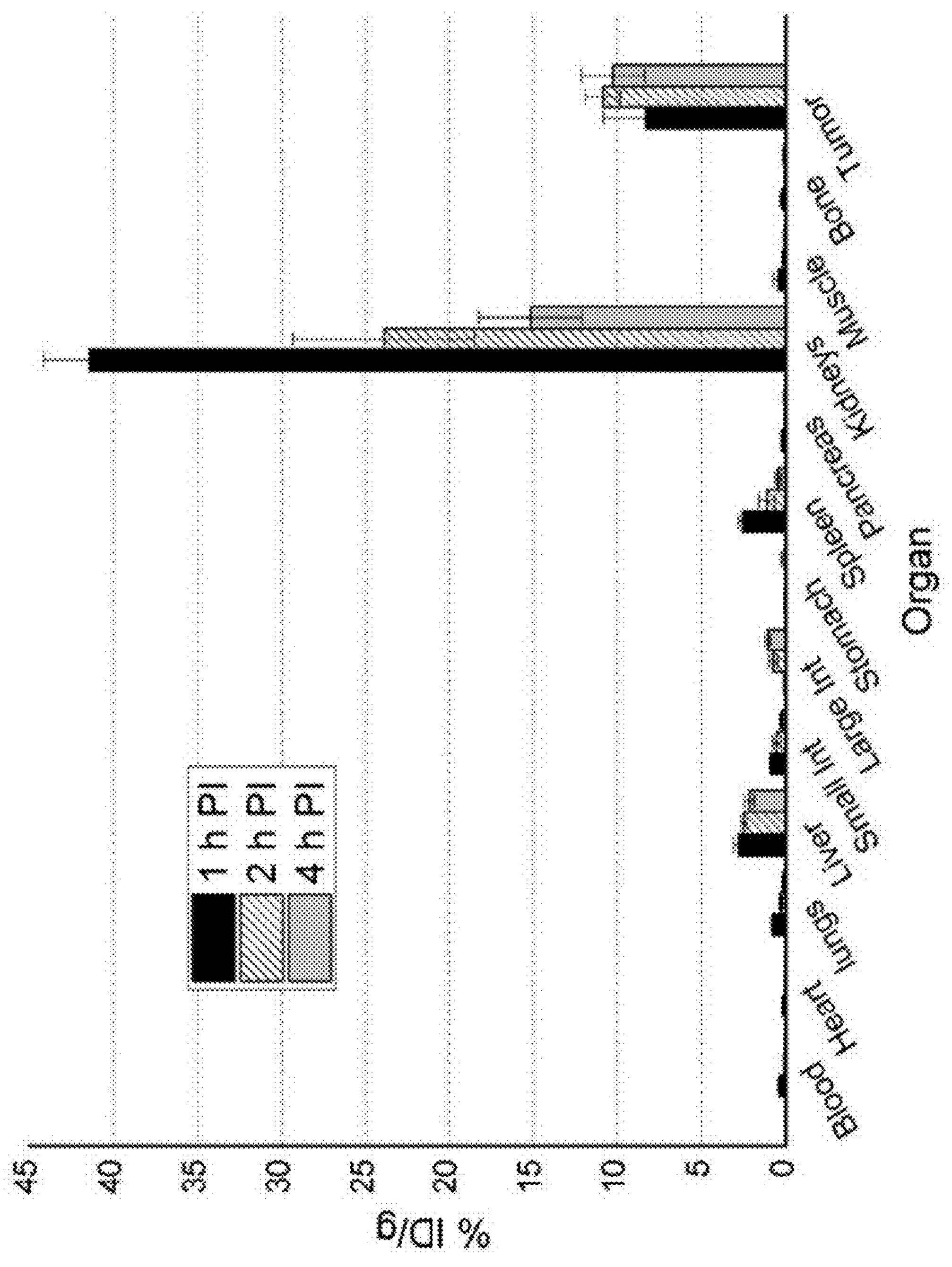
FIG. 3 provides the biodistribution of [$^{18}$F]RPS-041 (of the present technology) in LNCaP xenograft-tumor bearing mice. Mice (n=5 per time point) were sacrificed at 1 h (1 h PI), 2 h (2 h PI) and 4 h (4 h PI) post injection.

The imaging findings were corroborated in biodistribution studies where maximum tumor uptake was observed at 2 h post injection for both ligands (FIG. 2 and FIG. 3), with [$^{18}$F]RPS-040 reaching 14.30±2.49% ID/g (n=5) and [$^{18}$F]RPS-041 peaking at 10.86±1.03% ID/g (n=5). At this time point, uptake is also observed in the kidneys (60.94±8.06 and 23.93±5.45), the spleen (3.23±1.26 and 1.13±0.47) and the liver (4.72±0.93 and 2.51±0.21). Tumor-to-background ratios are plotted in FIG. 4. The ratios favor [$^{18}$F]RPS-041, which has a slightly lower tumor uptake than [$^{18}$F]RPS-040 at all time points, but considerably lower background signal. At 2 h post injection, contrast with [$^{18}$F]RPS-041 is two-fold greater than with [$^{18}$F]RPS-040.

To demonstrate that uptake was PSMA-mediated, five mice were co-injected with [$^{18}$F]RPS-040 and 2-phosphonomethylpentanedioic acid (2-PMPA), a potent PSMA inhibitor, and sacrificed at 1 h post injection. At this time point tumor uptake decreased from 12.69±1.56% ID/g (n=5) in the unblocked set of mice to 1.75±0.15% ID/g (n=5) in the set co-administered with 2-PMPA. Similar blocking was observed in the spleen (4.97±1.55% ID/g vs 0.32±0.05% ID/g) and kidneys (74.24±10.71% ID/g vs 5.95±1.65% ID/g) (FIG. 2), two other organs known to express PSMA in nude mice.

Comparison to [$^{68}$Ga]Ga-PSMA-HBED-CC.

Figures 5A, 5B, 5C:
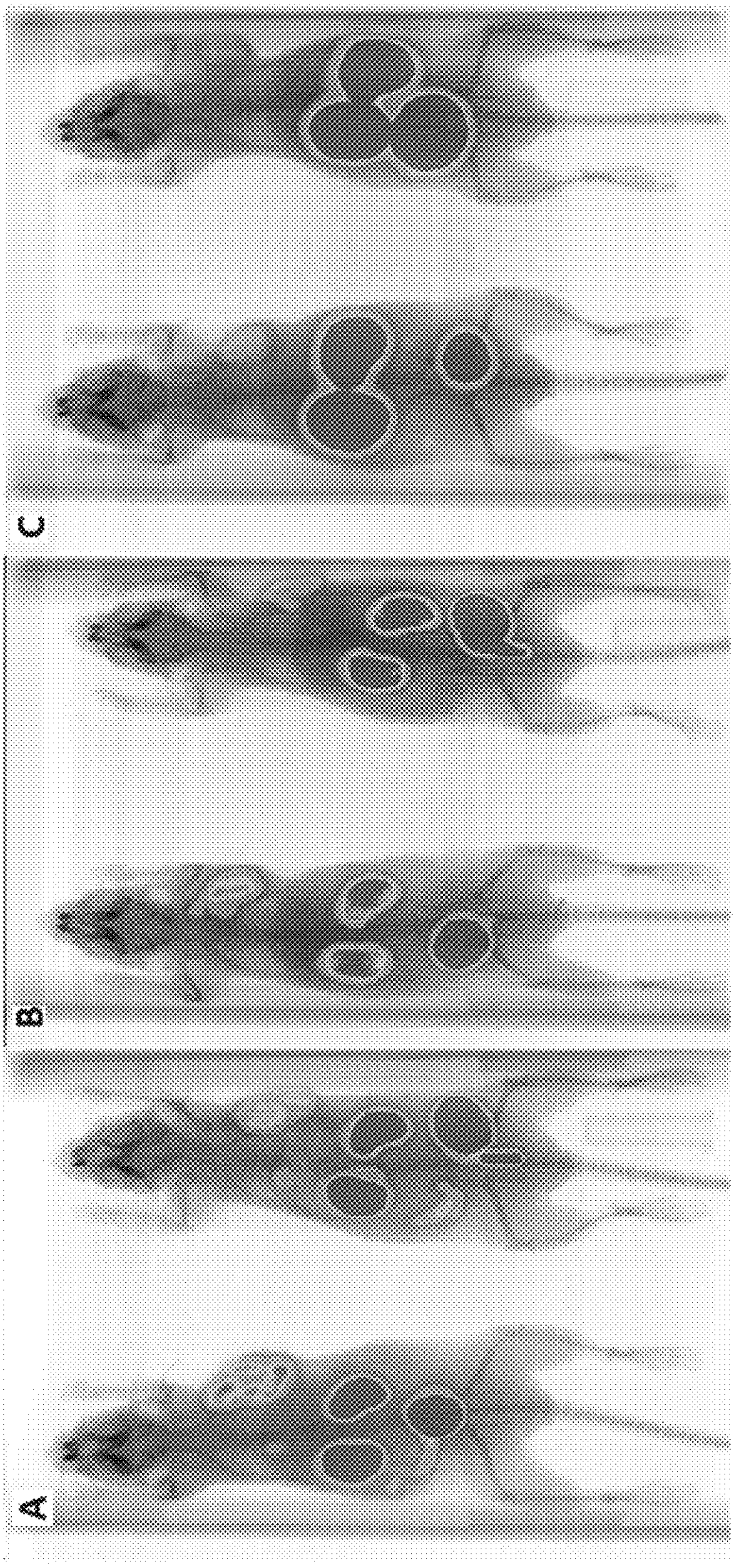
FIGS. 5A-5C provide the microPET/CT imaging of LNCaP xenograft-bearing nude mice with [$^{18}$F]RPS-040 (FIG. 5A), [$^{18}$F]RPS-041 (FIG. 5B), and [$^{68}$Ga]Ga-PSMA-HBED-CC (FIG. 5C). Mice were injected with 6.66-8.14 MBq (180-220 μCi) and imaged at 1 h post injection.

A comparison of pPET/CT images of [$^{18}$F]RPS-040 and [$^{18}$F]RPS-041 with [$^{68}$Ga]Ga-PSMA-HBED-CC shows significantly higher kidney uptake ($p<0.0002$) and lower tumor uptake ($p<0.0008$) in the gallium-68 tracer at 1 h post injection (FIG. 5). No uptake in the liver or intestine is evident in the [$^{68}$Ga]Ga-PSMA-HBED-CC.

Figures 6A, 6B, 6C:
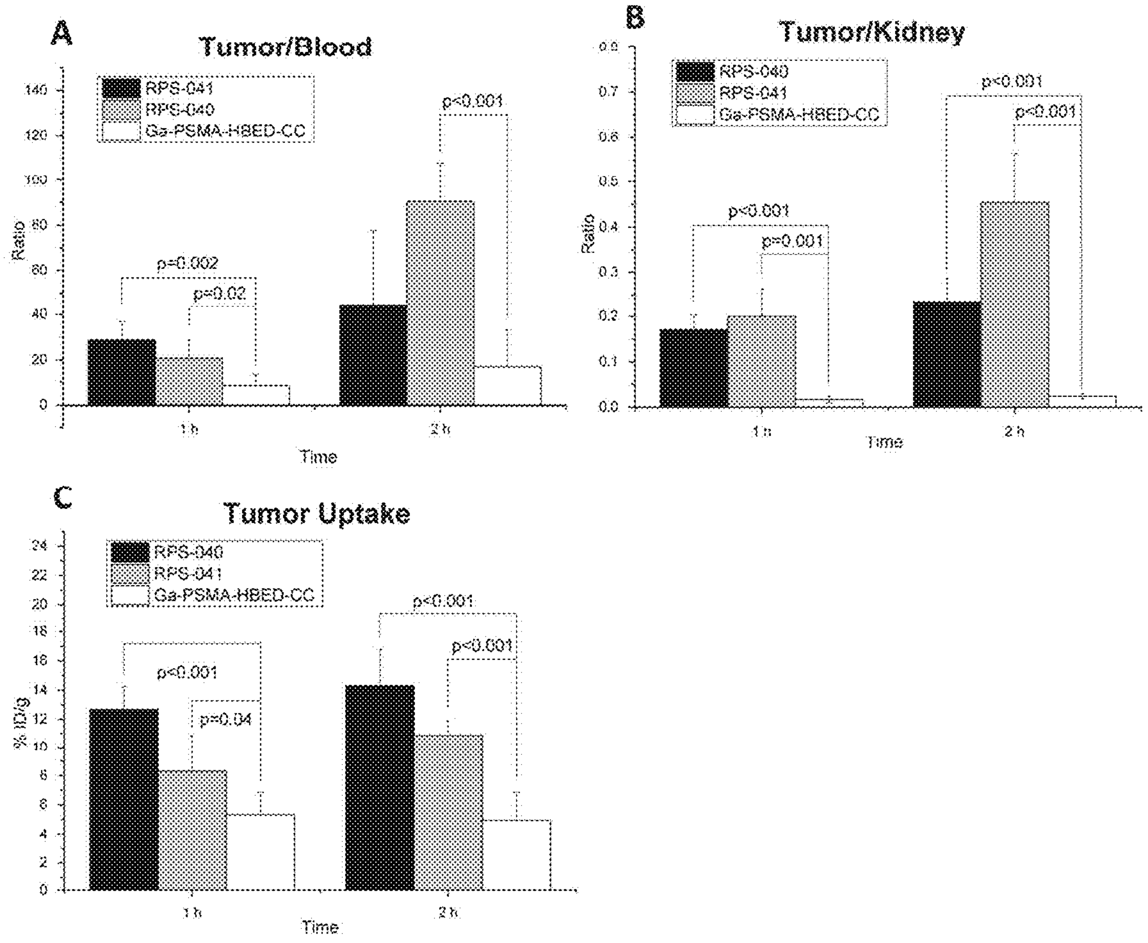
FIGS. 6A-6C provide a comparison of uptake in tumor, kidney, and blood between [$^{18}$F]RPS-040, [$^{18}$F]RPS-041 and [$^{68}$Ga]Ga-PSMA-HBED-CC. In particular, FIG. 6A provides the tumor-to-blood ratio at 1 h post injection and 2 h ([$^{68}$Ga]Ga-PSMA-HBED-CC) or 3 h post injection, FIG. 6B provides the tumor-to-kidney ratio, and FIG. 6C provides the tumor uptake.

These observations are reflected in the findings of ex vivo biodistributions. A recently reported study of [$^{68}$Ga]Ga-PSMA-HBED-CC demonstrated tumor uptake to be 5.81±1.67% ID/g at 1 h post injection and 6.27±1.44% ID/g at 3 h post injection (Nikolopoulou A, Amor-Coarasa A, Kelly J, Vallabhajosula V, and Babich J. Comparative evaluation of 68Ga-labeled urea-based PSMA ligands in LNCaP tumor bearing mice J Nucl Med May 1, 2015 vol. 56 no. supplement 3 114). At the time of maximum tumor uptake, therefore, [$^{18}$F]RPS-040 shows more than two-fold greater uptake than [$^{68}$Ga]Ga-PSMA-HBED-CC, while [$^{18}$F]RPS-041 is nearly two-fold greater. In comparison to both [$^{18}$F]RPS-040 and [$^{18}$F]RPS-041, activity in the blood was higher, while activity in the kidney (314.44±90.61 at 1 h; 207.97±58.38 at 3 h) and the spleen (31.73±14.09 at 1 h; 13.85±3.53 at 3 h) was significantly higher ($p<0.0002$ and $p<0.002$ respectively). These pharmacokinetics result in higher tumor uptake and enhanced tumor-to-background ratios for [$^{18}$F]RPS-040 and [$^{18}$F]RPS-041 relative to [$^{68}$Ga]Ga-PSMA-HBED-CC (FIG. 6).

At 1 h post injection, the tumor-to-blood ratio for [$^{18}$F]RPS-041 and [$^{18}$F]RPS-040 are more than two-fold and three-fold greater, respectively, than for [$^{68}$Ga]Ga-PSMA-HBED-CC, and these ratios continue to grow with time. The tumor-to-kidney ratio is even more striking, as [$^{18}$F]RPS-040 and [$^{18}$F]RPS-041 demonstrate ten- and twelve-fold greater contrast; once again, the relative contrast increases with time.

Discussion of Advantages of Present Technology

A prosthetic group strategy was envisioned for the synthesis and radiosynthesis of the six PSMA inhibitors. By this approach it was possible to overcome the interaction between fluoride and the urea protons which contributes to low yield and high variability in the direct fluorination of urea-based imaging probes. See Boiocchi M, Del Boca L, Gómez D E, Fabbrizzi L, Licchelli M, Monzani E. Nature of Urea-Fluoride Interaction: Incipient and Definitive Proton Transfer. J. Am. Chem. Soc. 2004, 126, 16507-16514. The application of the 2-[$^{18}$F]fluoroethylazide/Cu(I)-catalyzed click chemistry methodology to the radiosynthesis of compounds of the present technology was demonstrated to be a straightforward and reproducible route to high affinity ligands synthesized in good radiochemical yield.

Via a comparison of the substitution position on the phenyl ring, it was observed that tumor uptake is in the order 3-substitution>4-substitution>2-substitution for both Series One and Series Two of the representative compounds of the present technology. This order of preference was unexpected given previous SAR studies with a halogenated small molecule PSMA inhibitor, which indicated a strong preference for substitution at the 4-position (Maresca K P, Hillier S M, Femia F J, Barone D K C, Joyal J L, Zimmerman C N, Kozikowski A P, Barrett J A, Eckelman W C, Babich J W. A Series of Halogenated Heterodimeric Inhibitors of Prostate Specific Membrane Antigen (PSMA) as Radiolabeled Probes for Targeting Prostate Cancer. J. Med. Chem. 2009, 52, 347-357), and with (alkoxyphenyl)urea derivatives of Glu-urea-Lys, for which substitution at the 2-position led to higher affinity compounds (Tykvart J, Schimer J, Bařinková J, Pachl P, Poštová-Slavětinská L, Majer P, Konvalinka J, Šácha P. Rational design of urea-based glutamate carboxypeptidase II (GCPII) inhibitors as versatile tools for specific drug targeting and delivery. Bioorg. Med. Chem. 2014, 22, 4099-4108). It also did not correspond to the rank order of $IC_{50}$ values determined in LNCaP cells.

Figures 4A, 4B, 4C, 4D:
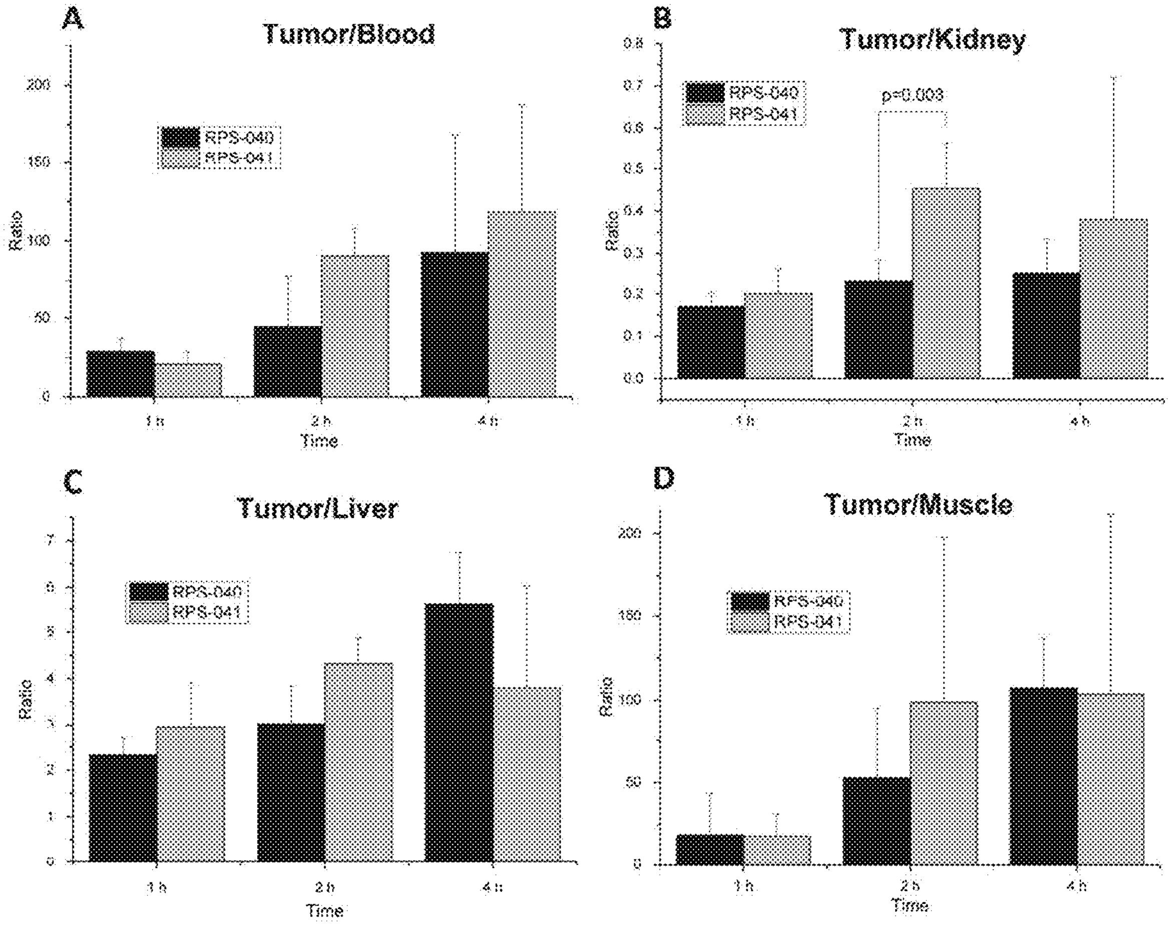
FIGS. 4A-4D provides the tumor-to-background ratios of [$^{18}$F]RPS-040 and [$^{18}$F]RPS-041 in LNCaP xenograft-tumor bearing mice, where FIG. 4A provides the tumor-to-blood ratio, FIG. 4B provides the tumor-to-kidney ratio, FIG. 4C provides the tumor-to-liver ratio, and FIG. 4D provides the tumor-to-muscle ratio. The large error bars in the tumor-to-muscle ratio are likely to be due to the low counts recorded in the muscle.

In spite of the increased tumor uptake of the 3-substituted [$^{18}$F]RPS-040 relative to 4-substituted [$^{18}$F]RPS-041, the clearance of [$^{18}$F]RPS-041 is more rapid, leading to greater image contrast and a higher tumor-to-background ratio at 2 h post injection (FIG. 1 and FIG. 4). The clearance of [$^{18}$F]RPS-038, the phenyl ether analogue of [$^{18}$F]RPS-041, is similarly more rapid than [$^{18}$F]RPS-043 (FIG. 1).

The imaging characteristics of each of the six representative [$^{18}$F]fluorinated compounds of the present technology compare favorably to [$^{68}$Ga]Ga-PSMA-HBED-CC, the most widely used diagnostic PET imaging agent for prostate cancer. In addition to the greater sensitivity and higher spatial resolution that fluorine-18 offers over gallium-68, the two- to three-fold higher tumor uptake is evident when images are compared in the same intensity scale (FIG. 5). The improved image quality is reinforced by the biodistribution studies with ligands [$^{18}$F]RPS-040 and [$^{18}$F]RPS-041, which showed significantly greater tumor-to-background and tumor-to-kidney ratios than [$^{68}$Ga]Ga-PSMA-HBED-CC (FIG. 6).

[$^{18}$F]DCFPyL, a second generation [$^{18}$F]fluorinated PSMA ligand currently undergoing clinical evaluation, has recently been studied in LNCaP tumor xenografts, and $SUV_{max}$ was reported to be 1.1±0.1 at 1 h post injection. See Bouvet V, Wuest M, Jans H-S, Janzen N, Genady A R, Valliant J F, Benard F, Wuest F. Automated synthesis of [18F]DCFPyL via direct radiofluorination and validation in preclinical prostate cancer models. EJNMMI Research 2016, 6:40. This is lower uptake than observed for each of the six representative $^{18}$F compounds of the present technology, for which SUV at 1 h post injection is estimated to range from 1.5 to 2.5 and $SUV_{max}$ in the tumor is calculated to range from approximately 1.5 to 2.9. Moreover, [$^{18}$F]DCFPyL is reported to have a tumor-to-blood ratio of 8.3 at 1 h post injection in LNCaP xenograft-bearing mice. At this same time point, the tumor-to-blood ratios for [$^{18}$F]RPS-040 and [$^{18}$F]RPS-041 are 28.8±8.06 and 20.78±7.87, respectively. By 4 h post injection, the prolonged tumor retention and rapid blood clearance drives the ratios to 92.93±75.67 and 118.4±69.4, respectively.

[$^{18}$F]DCFPyL was compared by pPET/CT imaging to the representative $^{18}$F compounds of the present technology in the same LNCaP xenograft-bearing mice. Clearance from the kidneys was rapid, but rapid tumor washout was also evident (FIG. 1). These pharmacokinetics contribute to a reduction in signal in the kidneys, but also to poorer tumor delineation than can be achieved with the RPS series. The in vitro binding of PSMA-targeting ligands to mouse kidney cells was reported to be at least two-fold greater than binding to human kidney cells, suggesting that rapid kidney clearance in pre-clinical mouse models of prostate cancer is not an essential requirement. In this light, the greater tumor uptake, longer tumor retention and greater tumor-to-blood ratios of [$^{18}$F]RPS-040 and [$^{18}$F]RPS-041 compared to [$^{18}$F]DCFPyL are favorable characteristics of these potential PET imaging agents.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound of Formula I (I)

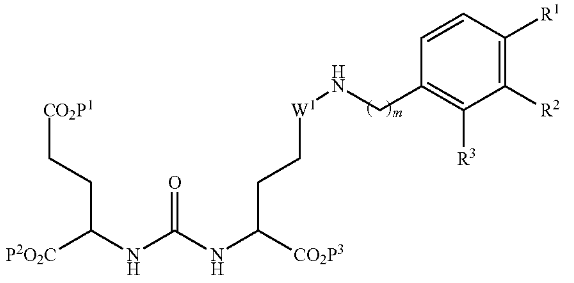

or a pharmaceutically acceptable salt thereof, wherein $P^1$, $P^2$, and $P^3$ are each independently H, methyl, benzyl, 4-methoxybenzyl, or tert-butyl;

$W^1$ is —C(O)— or —$(CH_2)_n$—NH—C(O)—;

one of $R^1$, $R^2$, and $R^3$ is

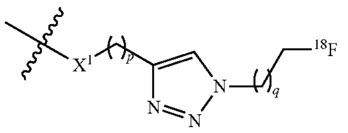

and the remaining two of $R^1$, $R^2$, and $R^3$ are each H;

$X^1$ is absent, O, S, or NH;

m is 0, 1, 2, or 3;

n is 1 or 2;

p is 0, 1, 2, or 3, provided that when p is 0 then $X^1$ is absent; and q is 1 or 2.

B. The compound of Paragraph A, wherein $P^1$, $P^2$, and $P^3$ are each independently H or tert-butyl.

C. The compound of Paragraph A or Paragraph B, wherein $P^1$, $P^2$, and $P^3$ are each independently H.

D. An intermediate for preparing a compound of any one of Paragraphs A-C, wherein the intermediate is of Formula II (II)

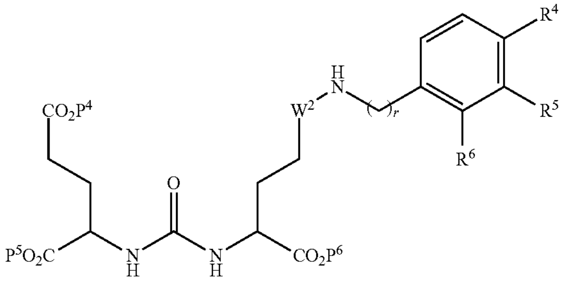

wherein $P^4$, $P^5$, and $P^6$ are each independently H, methyl, benzyl, 4-methoxybenzyl, or tert-butyl;

$W^2$ is —C(O)— or —$(CH_2)_n$—NH—C(O)—;

one of $R^4$, $R^5$, and $R^6$ is

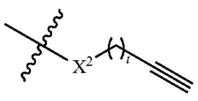

and the remaining two of $R^4$, $R^5$, and $R^6$ are each H;

$X^2$ is absent, O, S, or NH;

r is 0, 1, 2, or 3;

s is 1 or 2; and t is 0, 1, 2, or 3, provided that when t is 0 then $X^2$ is absent.

E. A composition comprising a compound of any one of Paragraphs A-D and a pharmaceutically acceptable carrier.

F. A pharmaceutical composition for detecting a mammalian tissue overexpressing prostate specific membrane antigen ("PSMA"), the composition comprising an effective amount of the compound of any one of Paragraphs A-C and a pharmaceutically acceptable carrier.

G. The pharmaceutical composition of Paragraph F, wherein the tissue includes one or more of glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, and prostate cancer.

H. A method comprising administering a compound of any one of Paragraphs A-C to a subject; and subsequent to the administering, detecting one or more of positron emission, gamma rays from positron emission and annihilation, and Cerenkov radiation due to positron emission.

I. The method of Paragraph H, wherein the method comprises administering an effective amount of the compound to the subject.

J. The method of Paragraph H or Paragraph I, wherein the subject is suspected of suffering from a mammalian tissue overexpressing prostate specific membrane antigen ("PSMA").

K. The method of Paragraph J, wherein the tissue comprises one or more of glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, and prostate cancer.

L. The method of any one of Paragraphs H-K, wherein administering the compound comprises parenteral administration.

M. A method of forming a compound of any one of Paragraphs A-C, wherein the method comprises contacting in the presence of a solvent a compound of Paragraph D, a copper salt, and an azide of Formula III (III)

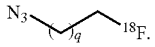

N. A compound of Formula IV (IV)

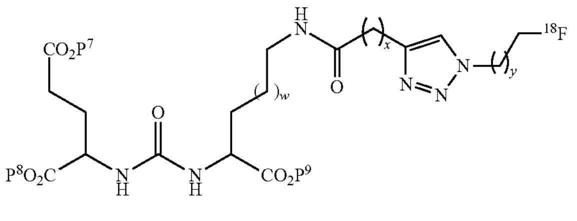

wherein $P^7$, $P^8$, and $P^9$ are each independently H, methyl, benzyl, 4-methoxybenzyl, or tert-butyl;

w is 1 or 2;

x is 0, 1, 2, or 3; and y is 1 or 2.

O. The compound of Paragraph N, wherein $P^7$, $P^8$, and $P^9$ are each independently H or tert-butyl.

P. The compound of Paragraph N or Paragraph 0, wherein $P^7$, $P^8$, and $P^9$ are each independently H.

Q. An intermediate for preparing a compound of any one of Paragraphs N-P, wherein the intermediate is of Formula V (V)

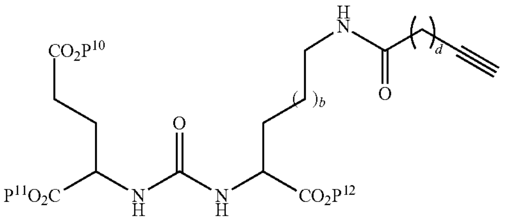

wherein $P^{10}$, $P^{11}$, and $P^{12}$ are each independently H, methyl, benzyl, 4-methoxybenzyl, or tert-butyl;

b is 1 or 2; and d is 0, 1, 2, or 3.

R. A composition comprising a compound of any one of Paragraphs N-Q and a pharmaceutically acceptable carrier.

S. A pharmaceutical composition for detecting a mammalian tissue overexpressing prostate specific membrane antigen ("PSMA"), the composition comprising an effective amount of the compound of any one of Paragraphs N-P and a pharmaceutically acceptable excipient.

T. The pharmaceutical composition of any one of Paragraphs N-P, wherein the tissue comprises one or more of glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, and prostate cancer.

U. A method comprising administering a compound of any one of Paragraphs N-P to a subject; and subsequent to the administering, detecting one or more of positron emission, gamma rays from positron emission and annihilation, and Cerenkov radiation due to positron emission.

V. The method of Paragraph U, wherein the method comprises administering an effective amount of the compound to the subject.

W. The method of Paragraph U or Paragraph V, wherein the subject is suspected of suffering from a mammalian tissue overexpressing prostate specific membrane antigen ("PSMA").

X. The method of Paragraph W, wherein the tissue comprises one or more of glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, and prostate cancer.

Y. The method of any one of Paragraphs U-X, wherein administering the compound comprises parenteral administration.

Z. A method of forming a compound of any one of Paragraphs N-P, wherein the method comprises contacting in the presence of a solvent a compound of Paragraph Q, a copper salt, and an azide of Formula VI (VI)

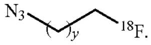

Other embodiments are set forth in the following claims, along with the full scope of equivalents to which such claims are entitled.

What is claimed is:

1. A compound that is

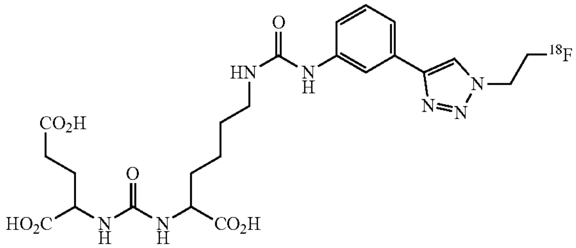 [SMILES: O=C(O)CCC(NC(=O)NC(CCCCNC(=O)Nc1cccc(-c2cn(CC[18F])nn2)c1)C(=O)O)C(=O)O]

or a pharmaceutically acceptable salt thereof.

2. A composition comprising a compound of claim 1 and a pharmaceutically acceptable carrier.

3. A pharmaceutical composition for detecting mammalian tissue overexpressing prostate specific membrane antigen (PSMA), the composition comprising an effective amount of the compound of claim 1 and a pharmaceutically acceptable carrier.

4. The pharmaceutical composition of claim 3, wherein the mammalian tissue comprises one or more of glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary gastric adenocarcinoma, primary colorectal adenocarcinoma, renal cell carcinoma, and prostate cancer.

5. A method comprising administering a compound of claim 1 to a subject; and subsequent to the administering, detecting one or more of positron emission, gamma rays from positron emission and annihilation, and Cerenkov radiation due to positron emission.

6. The method of claim 5, wherein the method comprises administering an effective amount of the compound to the subject.

7. The method of claim 5, wherein the subject is suspected of suffering from a mammalian tissue overexpressing prostate specific membrane antigen (PSMA).

8. The method of claim 7, wherein the mammalian tissue comprises one or more of glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary gastric adenocarcinoma, primary colorectal adenocarcinoma, renal cell carcinoma, and prostate cancer.

9. The method of claim 5, wherein the administering the compound comprises parenteral administration.

* * * * *